US008703696B2

(12) United States Patent
Lerchen et al.

(10) Patent No.: US 8,703,696 B2
(45) Date of Patent: Apr. 22, 2014

(54) DIPEPTOID PRODRUGS AND THE USE THEREOF

(75) Inventors: Hans-Georg Lerchen, Leverkusen (DE); Ursula Krenz, Leichlingen (DE); Joerg Keldenich, Wuppertal (DE); Nicole Diedrichs, Velbert (DE); Thomas Krahn, Hagen (DE); Claudia Hirth-Dietrich, Wuppertal (DE); Barbara Albrecht-Küpper, Wülfrath (DE)

(73) Assignee: Bayer Intellectual Property GmbH, Monheim (DE)

( * ) Notice: Subject to any disclaimer, the term of this patent is extended or adjusted under 35 U.S.C. 154(b) by 572 days.

(21) Appl. No.: 12/671,694

(22) PCT Filed: Jul. 23, 2008

(86) PCT No.: PCT/EP2008/006027
§ 371 (c)(1),
(2), (4) Date: Jul. 27, 2011

(87) PCT Pub. No.: WO2009/015811
PCT Pub. Date: Feb. 5, 2009

(65) Prior Publication Data
US 2011/0294718 A1 Dec. 1, 2011

(30) Foreign Application Priority Data
Aug. 1, 2007 (DE) .................. 10 2007 036 076

(51) Int. Cl.
*A61K 38/00* (2006.01)
*A61K 31/44* (2006.01)
*C07D 417/00* (2006.01)

(52) U.S. Cl.
USPC .................. 514/1.3; 514/342; 546/269.7

(58) Field of Classification Search
None
See application file for complete search history.

(56) References Cited

U.S. PATENT DOCUMENTS

| | | | |
|---|---|---|---|
| 4,052,510 A | 10/1977 | Simpson et al. | |
| 5,670,525 A | 9/1997 | Urbahns et al. | |
| 5,889,002 A | 3/1999 | Nielsen et al. | |
| 6,191,280 B1 | 2/2001 | Hamprecht et al. | |
| 6,586,441 B2 | 7/2003 | Borroni et al. | |
| 6,632,823 B1 | 10/2003 | Vernier et al. | |
| 6,693,102 B2 | 2/2004 | Stasch et al. | |
| 6,706,717 B2 | 3/2004 | Barrish et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 7,045,631 B2 | 5/2006 | Rosentreter et al. | |
| 7,078,417 B2 | 7/2006 | Rosentreter et al. | |
| 7,109,218 B2 | 9/2006 | Rosentreter et al. | |
| 7,129,255 B2 | 10/2006 | Rosentreter et al. | |
| 7,135,486 B1 | 11/2006 | Rosentreter et al. | |
| 7,173,036 B2 | 2/2007 | Sircar et al. | |
| 7,173,037 B2 | 2/2007 | Alonso-Alija et al. | |
| 7,186,716 B2 | 3/2007 | Wei et al. | |
| 7,674,825 B2 | 3/2010 | Alonso-Alija et al. | |
| 7,692,017 B2 | 4/2010 | Dinsmore et al. | |
| 7,705,043 B2 | 4/2010 | Alonso-Alija et al. | |
| 7,709,504 B2 | 5/2010 | Krahn et al. | |
| 7,781,470 B2 | 8/2010 | Alonso-Alija et al. | |
| 7,825,255 B2 | 11/2010 | Rosentreter et al. | |
| 7,855,219 B2 | 12/2010 | Rosentreter et al. | |
| 7,932,259 B2 | 4/2011 | Nakazato et al. | |
| 7,951,811 B2 | 5/2011 | Nakazato et al. | |
| 8,242,281 B2 | 8/2012 | Rosentreter et al. | |
| 8,304,412 B2 | 11/2012 | Nell et al. | |
| 8,420,825 B2 | 4/2013 | Vakalopoulos et al. | |
| 8,426,602 B2 | 4/2013 | Meibom et al. | |
| 8,440,700 B2 | 5/2013 | Nell et al. | |
| 2003/0232860 A1 | 12/2003 | Harada et al. | |
| 2004/0162427 A1 | 8/2004 | Rosentreter et al. | |
| 2004/0176446 A1 | 9/2004 | Alonso-Alija et al. | |
| 2005/0182105 A1 | 8/2005 | Nirschi et al. | |
| 2005/0227972 A1 | 10/2005 | Rosentreter et al. | |
| 2005/0250774 A1 | 11/2005 | Ono et al. | |
| 2006/0264432 A1 | 11/2006 | Rosentreter et al. | |
| 2007/0066630 A1 | 3/2007 | Palani et al. | |
| 2007/0293670 A1 | 12/2007 | Nakazato et al. | |
| 2008/0167321 A1 | 7/2008 | Kamboj et al. | |
| 2008/0269300 A1 | 10/2008 | Erguden et al. | |

(Continued)

FOREIGN PATENT DOCUMENTS

| | | | |
|---|---|---|---|
| EP | 0 608 565 A1 | 12/1993 | |
| JP | 09-132529 | 5/1997 | |
| JP | 10-324687 | 12/1998 | |
| JP | 2003-183254 | 7/2003 | |
| WO | 95/34563 | 12/1995 | |
| WO | 97/27177 A2 | 7/1997 | |
| WO | 99/03861 A1 | 1/1999 | |
| WO | 02/48115 A2 | 6/2002 | |
| WO | 02/50071 A1 | 6/2002 | |
| WO | WO03/053441 | * 7/2003 | ......... A61K 31/4418 |

(Continued)

OTHER PUBLICATIONS

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

(Continued)

*Primary Examiner* — Marcela M Cordero Garcia
(74) *Attorney, Agent, or Firm* — Karen B. King; Thomas C. Blankinship

(57) ABSTRACT

The present application relates to prodrug derivatives of 2-amino-6-({[2-(4-chlorophenyl)-1,3-thiazol-4-yl]methyl}thio)-4-[4-(2-hydroxyethoxy)phenyl]pyridine-3,5-dicarbonitrile, processes for their preparation, their use for the treatment and/or prophylaxis of diseases, and their use for the manufacture of medicaments for the treatment and/or prophylaxis of diseases, especially of cardiovascular disorders.

8 Claims, No Drawings

(56) References Cited

U.S. PATENT DOCUMENTS

| | | |
|---|---|---|
| 2009/0221649 A1 | 9/2009 | Krahn et al. |
| 2010/0009973 A1 | 1/2010 | Rhodes et al. |
| 2010/0022544 A1 | 1/2010 | Nell et al. |
| 2010/0048641 A1 | 2/2010 | Nell et al. |
| 2010/0069363 A1 | 3/2010 | Nell et al. |
| 2010/0093728 A1 | 4/2010 | Nell et al. |
| 2011/0130377 A1 | 6/2011 | Nell et al. |
| 2011/0136871 A1 | 6/2011 | Hübsch et al. |
| 2011/0207698 A1 | 8/2011 | Meibom et al. |
| 2011/0237629 A1 | 9/2011 | Meibom et al. |

FOREIGN PATENT DOCUMENTS

| | | |
|---|---|---|
| WO | 03/091246 | 11/2003 |
| WO | 2004/014372 A1 | 2/2004 |
| WO | 2004/054505 A2 | 7/2004 |
| WO | 2005/007647 | 1/2005 |
| WO | 2007/073855 | 7/2007 |
| WO | 2008/008059 | 1/2008 |

OTHER PUBLICATIONS

Avila, et al.: Al-, A2A- and A3-subtype adenosine receptors modulate intraocular pressure in the mouse, British Journal of Pharmacology, 2001, 134:241-245.

Barnaby, et al.:"Structure-Activity Relationship Study of Prion Inhibition by 2-Aminopyridine-3,5-dicarbonitrile-Based Compounds: Parallel Synthesis, Bioactivity, and in Vitro Pharmacokinetics," J. Med. Chem., 2007, 50:65-73.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Beukers, et al.:"New, Non-Adenosine, High-Potency Agonists for the Human Adenosine A2B Receptor with an Improved Selectivity Profile Compared to the Reference Agonist N-Ethylcarboxamidoadenosine," Journal of Medicinal Chemistry, Jul. 15, 2004, 47(15): 3707-3709.

Bundgaard:"Design of Prodrugs: Bioreversible Derivatives for Various Functional Groups and Chemical Entities," Elsevier Science Publishers B.V., 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods:A New Approach to the Arndt-Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyanopyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5-Dicyanopyridine-2(1H)-thionene," Chemistry of Heterocyclic Compounds, 1998, 34(2):188-194.

Dyachenko:"Cyclohexanecarbaldehyde in Multicomponent Syntheses of Functionalized Cyclohexyl-Substituted Acrylonitriles, 4H-Chalcogenopyrans, 1,4-Dihydropyridines, and Pyridines," Russian Journal of General Chemistry, 2006, 76(2):282-291.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b]pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using α,β-Unsaturated Nitriles: Facile Synthesis of Pyridine Derivatives," Synthesis Communications, Jul. 1981, pp. 531-533.

Klotz, et al.:"Comparative Pharmacology of Human Adenosine Receptor Subtypescharacterization of Stably Transfected Receptors in CHO Cells," Naunyn-Schmiedeberg's Arch Pharmacol, 1998, 357:1-9.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Olah, et al.:"Cloning, Expression, and Characterization of the Unique Bovine A1 Adenosine Receptor," Journal of Biological Chemistry, May 25, 1992, 267(15):10764-10770.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Poulsen, et al.:"Adenosine Receptors: New Opportunities for Future Drugs," Bioorganic & Medicinal Chemistry, Jan. 8, 1998, 6(6): 619-641.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica γ Bioquimica, 1984, 80(3):268-72, English language abstract retrieved from CAPLUS Accession No. 1985:437345, CAPLUS Document No. 103:37345, EPO Document No. XP002202945.

(56) References Cited

OTHER PUBLICATIONS

Quintela, et al.:"Synthesis, Antihistaminic and Cytotoxic Activity of Pyridothieno- and Pyridodithienotriazines", Eur. J. Med. Chem, 1998, 33:887-897.
Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.
Rosenman:"Do Environmental Effects on Human Emotions Cause Cardiovascular Disorders?," Acta Physiologica Scandinavica, Supplement,1997, 161/640 (133-136), abstract retrieved from EMBASE Accession No. 97358868.
Ruhe, et al.:"Use of Antioxidant Nutrients in the Prevention and Treatment of Type 2 Diabetes," Journal of the American College of Nutrition, 2001, 20(5): 363S-369S.
Shams, et al.:"Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.
Sheridan:"The Most Common Chemical Replacements in Drug-Like Compounds," J Chem. Inf. Comput. Sci., 2002, 42:103-108.
Suttner, et al.:"The Heart in the Elderly Critically III Patient," Curr. Opin. Crit. Care, Oct. 2002, 8(5):389-94, abstract retrieved from Medline Accession No. 2002495386, PubMed ID: 12357105.
Szydlowski, et al.:"Biological Role of Chromium," Diabetologia Polska, 2003, 10(3):365-370, English language abstract retrieved from EMBASE Accession No. 2004016455.
Vasudevan A. et al., "Aminopiperidine indazoles as orally efficacious melanin concentrating hormone receptoer-1 antagonists," Bioorg. Med. Chem. Lett. 2005, 15 (23), 5293-5297.
Vippagunta, et al.:"Crystalline Solids," Advanced Drug Delivery Reviews, May 16, 2001, 48(1):3-26.
West:"Solid State Chemistry and its Applications," Wiley, New York, 1988, pp. 358 & 365.
Ye, et al.:Organic Synthesis with α-Diazocarbonyl Compounds, Chem. Rev. 1994, 94:1091-1160.
Yu, et al:"Physical Characterization of Polymorphic Drugs: An Integrated Characterization Strategy," Pharmaceutical Science & Technology Today, Jun. 1998, 1(3):118-127.
Zhu, G. et al., "Design and synthesis of pyridine-pyrazolopyridine-based inhibitors of protein kinase B/Akt," Bioorg. Med. Chem. 2007, 15 (6), 2441-2452.
Nielsen, et al.: "Dipeptide model prodrugs for the intestinal oligopeptide transporter. Affinity for an transport via hPepT1 in the human intestinal Caco-2 cell line," J. of Controlled Release 2001, 76:129-138.
U.S. Appl. No. 11/607,262, filed Dec. 27, 2011, published as US 2007-0213372.
U.S. Appl. No. 11/661,820, filed Mar. 10, 2008, published as US 2008-0269300.
U.S. Appl. No. 12/516,939, filed Nov. 24, 2009 published as US 2010-0069363.
U.S. Appl. No. 12/440,423, filed Dec. 23, 2009 published as US 2010-0093728.
U.S. Appl. No. 12/516,917, filed May 29, 2009, published as US 2010-0022544.
U.S. Appl. No. 12/671,019, filed Jan. 27, 2010, published as US 2011-0130377.
U.S. Appl. No. 12/922,172, filed May 16, 2011 published as US 2011-0207698.
U.S. Appl. No. 12/995,028, filed Feb. 16, 2011 published as US 2011-0207698.
U.S. Appl. No. 13/132,991, filed Aug. 23, 2011 published as US 2011-0294719.
U.S. Appl. No. 12/697,000, filed Jan. 29, 2010, published as US 2010-0197609.
U.S. Appl. No. 13/210,889, filed Aug. 16, 2011.
Clark, Kenneth, et al., "Potential of adenosine receptor agonists for the prevention and treatment of coronary artery disease and acute myocardial infarction," Emerging Drugs, 2000, 5(1):89-108.

* cited by examiner

DIPEPTOID PRODRUGS AND THE USE THEREOF

The present application relates to prodrug derivatives of 2-amino-6-({[2-(4-chlorophenyl)-1,3-thiazol-4-yl]methyl}thio)-4-[4-(2-hydroxyethoxy)phenyl]pyridine-3,5-dicarbonitrile, processes for their preparation, their use for the treatment and/or prophylaxis of diseases, and their use for the manufacture of medicaments for the treatment and/or prophylaxis of diseases, especially of cardiovascular disorders.

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393-2404 (2004)]. In order to achieve an optimal profile of effects it is necessary in this connection for the design of the prodrug residue as well as the desired mechanism of liberation to conform very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985.

Adenosine, a purine nucleoside, is present in all cells and is released under a large number of physiological and pathophysiological stimuli. Adenosine is produced inside cells on degradation of adenosine 5'-monophosphate (AMP) and S-adenosylhomocysteine as intermediate, but can be released from the cell and then exerts, by binding to specific receptors, effects as hormone-light substance or neurotransmitter. Essential functions in particular in excitable and/or working cells in various tissues are influenced by adenosine A1 receptors [cf. K. A. Jacobson and Z.-G. Gao, *Nat. Rev. Drug Discover.* 5, 247-264 (2006)].

The compound 2-amino-6-({[2-(4-chlorophenyl)-1,3-thiazol-4-yl]methyl}thio)-4-[4-(2-hydroxy-ethoxy)phenyl]pyridine-3,5-dicarbonitrile [compound (A)] is an orally active adenosine A1 receptor agonist and is currently undergoing in-depth clinical testing as a possible novel active pharmaceutical ingredient for the prevention and therapy in particular of cardiovascular disorders [*WHO Drug Information Vol.* 20, No. 2 (2006); for preparation and use, see WO 03/053441, example 6].

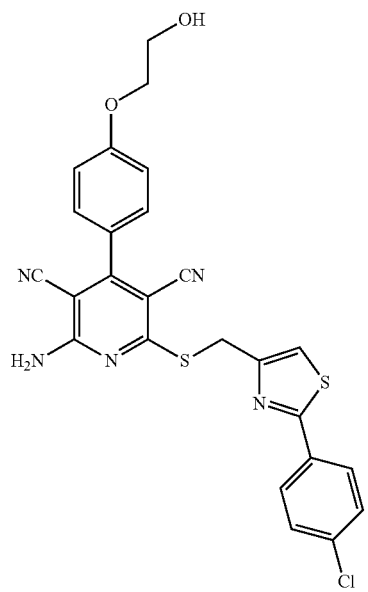

(A)

However, compound (A) has only a limited solubility in water, physiological media and organic solvents, and an only low bioavailability after oral administration of a suspension of crystalline material. On the one hand, this allows intravenous administration of the active ingredient only in very low dosages; infusion solutions based on physiological saline solutions can be produced only with difficulty with conventional solubilizers. On the other hand formulation in tablet form is difficult. It was therefore an object of the present invention to identify derivatives or prodrugs of compound (A) which have an improved solubility in the media mentioned and/or an improved bioavailability after oral administration and, at the same time, allow controlled liberation of the active ingredient (A) in the patient's body after administration. In addition, further areas of therapeutic use of this active ingredient could be opened up by an improved possibility of intravenous administration.

A review of prodrug derivatives based on carboxylic esters and possible properties of such compounds is given for example in K. Beaumont et al., *Curr. Drug Metab.* 4, 461-485 (2003).

The present invention relates to compounds of the general formula (I)

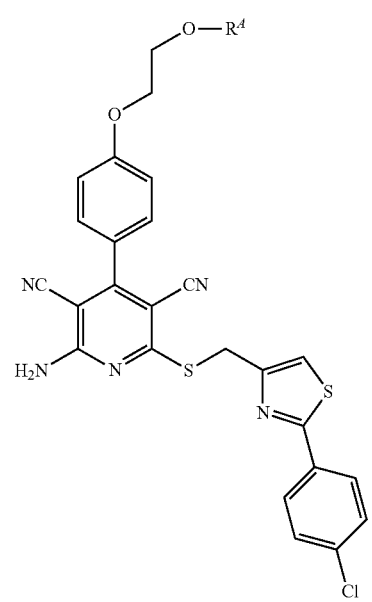

(I)

in which
$R^4$ is a group of the formula

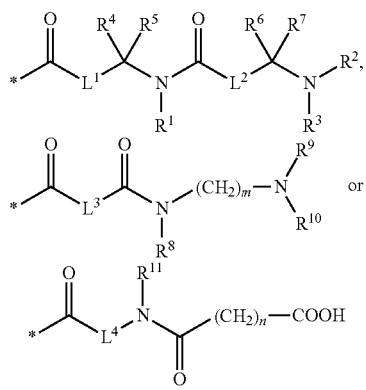

in which
* means the point of linkage to the O atom,
$L^1$ and $L^2$ are independently of one another a bond or —$CH_2$—,
$R^1$, $R^2$ and $R^3$ are independently of one another hydrogen or methyl,
$R^4$ and $R^6$ are identical or different and are independently of one another hydrogen or the side group of a natural α-amino acid or its homologs or isomers,
$R^5$ and $R^7$ are independently of one another hydrogen or methyl,
$L^3$ is straight-chain or branched ($C_2$-$C_4$)-alkanediyl which is additionally substituted by amino,
$R^8$, $R^9$ and $R^{10}$ are independently of one another hydrogen or methyl,
m is the number 2, 3, 4, 5 or 6,
$L^4$ is straight-chain or branched ($C_2$-$C_4$)-alkanediyl, which is additionally substituted by carboxyl,
$R^{11}$ is hydrogen or methyl,
and
n is the number 1, 2, 3 or 4,
and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Besides monosalts, the present invention also includes where appropriate possible polysalts such as di- or trisalts.

Physiologically acceptable salts of the compounds according to the invention include acid addition salts of mineral acids, carboxylic acids and sulphonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of usual bases such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, choline, dicyclohexylamine, dimethylaminoethanol, procain, dibenzylamine, morpholine, N-methylmorpholine, arginine, lysine, ethylenediamine, piperidine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

In the context of the present invention, the substituents have the following meaning unless otherwise specified:

($C_2$-$C_4$)-Alkanediyl is in the context of the invention a straight-chain or branched divalent alkyl radical having 2 to 4 carbon atoms. A straight-chain alkanediyl radical having 2 to 4 carbon atoms is preferred. Examples which may be preferably mentioned are: ethane-1,2-diyl (1,2-ethylene), ethane-1,1-diyl, propane-1,3-diyl (1,3-propylene), propane-1,1-diyl, propane-1,2-diyl, propane-2,2-diyl, butane-1,4-diyl (1,4-butylene), butane-1,2-diyl, butane-1,3-diyl, butane-2,3-diyl. The alkanediyl radical is additionally substituted in the case of the group $L^3$ by an amino group and in the case of the group $L^4$ by a carboxyl group.

The side group of an α-amino acid in the meaning of $R^4$ and $R^6$ encompasses both the side groups of naturally occurring α-amino acids and the side groups of homologs and isomers of these α-amino acids. The α-amino acid may in this connection have both the L and the D configuration or else be a mixture of the L form and D form. Examples of side groups which may be mentioned are: methyl (alanine), propan-2-yl (valine), propan-1-yl (norvaline), 2-methylpropan-1-yl (leucine), 1-methylpropan-1-yl (isoleucine), butan-1-yl (norleucine), tert-butyl(2-tert-butylglycine), phenyl (2-phenylglycine), benzyl (phenylalanine), p-hydroxybenzyl (tyrosine), indol-3-ylmethyl (tryptophan), imidazol-4-ylmethyl (histidine), hydroxymethyl (serine), 2-hydroxyethyl (homoserine), 1-hydroxyethyl (threonine), mercaptomethyl (cysteine), methylthiomethyl (S-methylcysteine), 2-mercaptoethyl (homocysteine), 2-methylthioethyl (methionine), carbamoylmethyl (asparagine), 2-carbamoylethyl (glutamine), carboxymethyl (aspartic acid), 2-carboxyethyl (glutamic acid), 4-aminobutan-1-yl (lysine), 4-amino-3-hydroxybutan-1-yl (hydroxylysine), 3-aminopropan-1-yl (ornithine), 3-guanidinopropan-1-yl (arginine), 3-ureidopropan-1-yl (citrulline). Preferred α-amino acid side groups in the meaning of $R^4$ are methyl (alanine), propan-2-yl (valine), propan-1-yl (norvaline), 2-methylpropan-1-yl (leucine), 1-methylpropan-1-yl (isoleucine), butan-1-yl (norleucine), benzyl (phenylalanine), p-hydroxybenzyl (tyrosine), imidazol-4-ylmethyl (histidine), hydroxymethyl (serine), 1-hydroxyethyl (threonine), carbamoylmethyl (asparagine), 2-carbamoylethyl (glutamine). Preferred α-amino acid side groups in the meaning of $R^6$ are imidazol-4-ylmethyl (histidine), 4-aminobutan-1-yl (lysine), 3-aminopropan-1-yl (ornithine), 2-aminoethyl (2,4-diaminobutyric acid), aminomethyl (2,3-diaminopropionic acid), 3-guanidinopropan-1-yl (arginine). The L configuration is preferred in each case.

Preference is given to compounds of the formula (I) in which
$R^4$ is a group of the formula

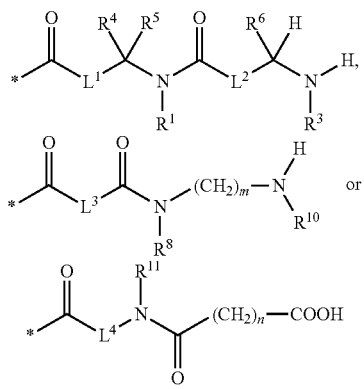

in which
* means the point of linkage to the O atom,
$L^1$ is a bond,
$L^2$ is a bond or —CH$_2$—,
$R^1$ and $R^3$ are independently of one another hydrogen or methyl,
$R^4$ is hydrogen, methyl, propan-2-yl, propan-1-yl, 2-methylpropan-1-yl, 1-methylpropan-1-yl, butan-1-yl, benzyl, p-hydroxybenzyl, imidazol-4-ylmethyl, hydroxymethyl, 1-hydroxyethyl, carbamoylmethyl or 2-carbamoylethyl,
$R^6$ is hydrogen, imidazol-4-ylmethyl, 4-aminobutan-1-yl, 3-aminopropan-1-yl, 2-aminoethyl, aminomethyl or 3-guanidinopropan-1-yl,
$L^3$ is straight-chain (C$_2$-C$_4$)-alkanediyl which is additionally substituted by amino,
$R^8$ and $R^{10}$ are independently of one another hydrogen or methyl,
m is the number 2, 3 or 4,
$L^4$ is straight-chain (C$_2$-C$_4$)-alkanediyl which is additionally substituted by carboxyl,
$R^{11}$ is hydrogen or methyl,
and
n is the number 2, 3 or 4,
and the salts, solvates and solvates of the salts thereof.

Particular preference is given to compounds of the formula (I) in which
$R^4$ is a group of the formula

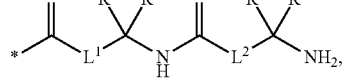

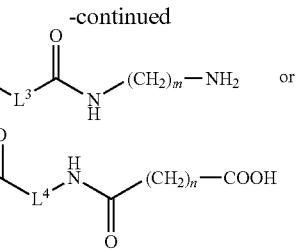

in which
* means the point of linkage to the O atom,
$L^1$ and $L^2$ are each a bond,
$R^4$ is hydrogen, methyl, propan-2-yl, propan-1-yl, 2-methylpropan-1-yl, 1-methylpropan-1-yl, butan-1-yl, benzyl, p-hydroxybenzyl, imidazol-4-ylmethyl, hydroxymethyl, 1-hydroxyethyl, carbamoylmethyl or 2-carbamoylethyl,
$R^6$ is imidazol-4-ylmethyl, 4-aminobutan-1-yl, 3-aminopropan-1-yl, 2-aminoethyl, aminomethyl or 3-guanidinopropan-1-yl,
$L^3$ is a group of the formula —CH(NH$_2$)—CH$_2$—, —CH$_2$—CH(NH$_2$)—, —CH$_2$—CH(NH$_2$)—CH$_2$—, —CH(NH$_2$)—CH$_2$—CH$_2$— or —CH$_2$—CH$_2$—CH(NH$_2$)—,
m is the number 2, 3 or 4,
$L^4$ is a group of the formula —CH$_2$—CH(COOH)— or —CH$_2$—CH$_2$—CH(COOH)—, in which
** represents the point of linkage to the adjoining carbonyl group,
and
n is the number 2 or 3,
and the salts, solvates and solvates of the salts thereof.

Very particular preference is given to compounds of the formula (I) in which
$R^4$ is a group of the formula

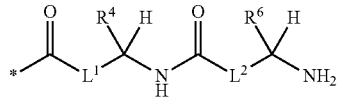

in which
* means the point of linkage to the O atom,
$L^1$ and $L^2$ are each a bond,
$R^4$ is hydrogen, methyl, propan-2-yl, 2-methylpropan-1-yl, benzyl, hydroxymethyl or 1-hydroxyethyl,
and
$R^6$ is imidazol-4-ylmethyl, 4-aminobutan-1-yl, 3-aminopropan-1-yl, 2-aminoethyl, aminomethyl or 3-guanidinopropan-1-yl,
and the salts, solvates and solvates of the salts thereof.

Very particular preference is also given to compounds of the formula (I) in which
$R^4$ is a group of the formula

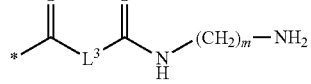

in which

* means the point of linkage to the O atom, $L^3$ is a group of the formula —CH(NH$_2$)—CH$_2$—, —CH$_2$—CH(NH$_2$)—, —CH(NH$_2$)—CH$_2$—CH$_2$— or —CH$_2$—CH$_2$—CH(NH$_2$)—, and m is the number 2 or 3, and the salts, solvates and solvates of the salts thereof.

The invention further relates to a process for preparing the compounds according to the invention of the formula (I), characterized in that the compound (A)

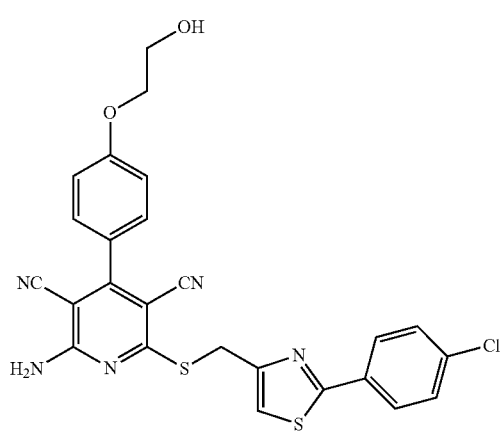

(A)

either

[A] is esterified in an inert solvent in the presence of a condensing agent initially with a carboxylic acid of the formula (II), (III) or (IV)

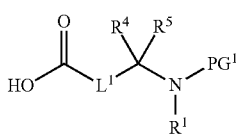

(II)

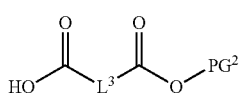

(III)

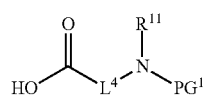

(IV)

in which $L^1$, $L^3$, $L^4$, $R^1$, $R^4$, $R^5$ and $R^{11}$ each have the meanings indicated above, and $PG^1$ is a temporary amino protective group such as, for example, tert-butoxycarbonyl and $PG^2$ is a temporary carboxyl protective group such as, for example, tert-butyl, to give compounds of the formula (V), (VI) or (VII),

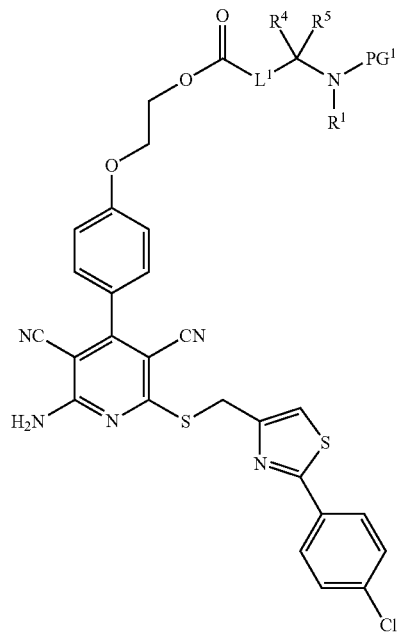

(V)

(VI)

(VII)

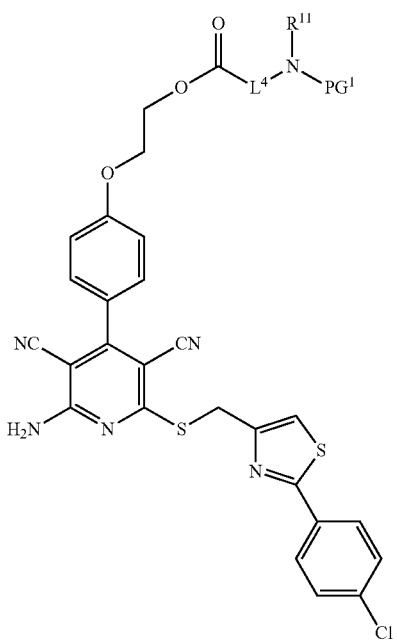

in which $L^1$, $L^3$, $L^4$, $R^1$, $R^4$, $R^5$, $R^{11}$, $PG^1$ and $PG^2$ each have the meanings indicated above, then, after elimination of the protective group $PG^1$ or $PG^2$, is coupled in an inert solvent in the presence of a condensing agent in the case of compound (V) with a compound of the formula (VIII), in the case of compound (VI) with a compound of the formula (IX) and in the case of compound (VII) with a compound of the formula (X)

(VIII)

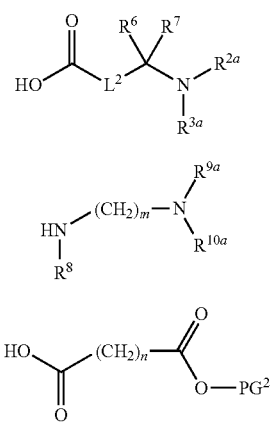

(IX)

(X)

in which $L^2$, $R^6$, $R^7$, $R^8$, $PG^2$, m and n each have the meanings indicated above, and $R^{2a}$ and $R^{3a}$, and $R^{9a}$ and $R^{10a}$, are in each case identical or different and have the meanings of respectively $R^2$, $R^3$, $R^9$ and $R^{10}$ indicated above, or are a temporary amino protective group such as, for example, tert-butoxycarbonyl, and subsequently protective groups which are present where appropriate are removed again, or

[B] is coupled in an inert solvent in the presence of a condensing agent with a compound of the formula (X), (XII) or (XIII)

(XI)

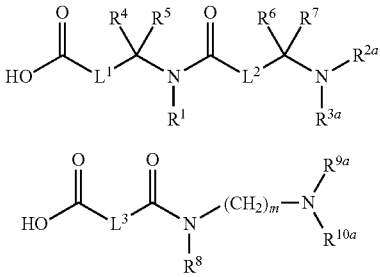

(XII)

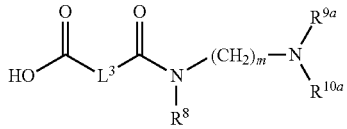

(XIII)

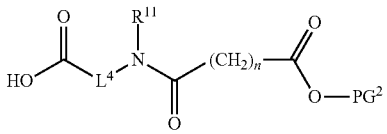

in which $L^1$, $L^2$, $L^3$, $L^4$, $R^1$, $R^4$, $R^5$, $R^6$, $R^7$, $R^8$, $R^{11}$, m and n each have the meanings indicated above, $R^{2a}$ and $R^{3a}$, and $R^{9a}$ and $R^{10a}$, are in each case identical or different and have the meanings of respectively $R^2$, $R^3$, $R^9$ and $R^{10}$ indicated above, or are a temporary amino protective group such as, for example, tert-butoxycarbonyl, and $PG^2$ is a temporary carboxyl protective group such as, for example, tert-butyl, and subsequently protective groups which are present where appropriate are removed again, and the resulting compounds of the formula (I) are converted where appropriate with the appropriate (i) solvents and/or (ii) acids or bases into the solvates, salts and/or solvates of the salts thereof.

The transformation (A)→(I) thus takes place either by sequential coupling of the individual carboxylic acid or amine components which are suitably protected where appropriate (process variant [A]) or by direct acylation with a suitably protected dipeptoid derivative (process variant [B]). The coupling reactions (ester or amide formation) are in this case carried out by known methods of peptide chemistry [cf., for example, M. Bodanszky, *Principles of Peptide Synthesis*, Springer-Verlag, Berlin, 1993; H.-D. Jakubke and H. Jeschkeit, *Aminosäuren, Peptide, Proteine*, Verlag Chemie, Weinheim, 1982].

Examples of inert solvents for the coupling reactions are ethers such as diethyl ether, tert-butyl methyl ether, dioxane, tetrahydrofuran, glycol dimethyl ether or diethylene glycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichloro-ethane, trichloroethylene or chlorobenzene, or other solvents such as acetone, ethyl acetate, pyridine, dimethyl sulfoxide, dimethylformamide, N,N'-dimethylpropyleneurea (DMPU), N-methylpyrrolidone (NMP) or acetonitrile. It is likewise possible to use mixtures of the solvents mentioned. Dichloromethane, dimethylformamide or mixtures of these two solvents are preferred.

Examples of suitable condensing agents in these coupling reactions are carbodiimides such as N,N'-diethyl-, N,N'-dipropyl-, N,N'-diisopropyl-, N,N'-dicyclohexylcarbodiimide (DCC) or N-(3-dimethylaminoisopropyl)-N'-ethylcarbodiimide hydrochloride (EDC), phosgene derivatives such as N,N'-carbonyldiimidazole (CDI), 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, or isobutyl chloroformate, propanephosphonic anhydride, diethyl cyanophosphonate, bis-(2-oxo-3-oxazolidinyl)phosphoryl chloride, benzotriazol-1-yloxytris(dimethylamino)phosphonium hexafluorophosphate, benzotriazol-1-yloxytris(pyrrolidino)phosphonium hexafluorophosphate (PyBOP), O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU) or O-(1H-6-chlorobenzotriazol-1-yl)-1,1,3,3-tetramethyluronium tetrafluoroborate (TCTU), where appropriate in combination with further auxiliaries such as 1-hydroxybenzotriazole (HOBt) or N-hydroxysuccinimide (HOSu), and as bases are alkali metal carbonates, e.g. sodium or potassium carbonate, or organic bases such as triethylamine, N-methylmorpholine, N-methylpiperidine, N,N-diisopropylethylamine or 4-N,N-dimethylaminopyridine. N-(3-Dimethylaminoisopropyl)-N'-ethylcarbodiimide hydrochloride (EDC) in combination with 4-N,N-dimethylaminopyridine is preferably employed for ester deformation. N-(3-Dimethylaminoisopropyl)-N'-ethylcarbodiimide hydrochloride (EDC) in combination with 1-hydroxybenzotriazole (HOBt) or N-hydroxysuccinimide (HOSu) and, where appropriate, a base such as N,N-diisopropylethylamine is preferably used for amide formation.

The couplings are generally carried out in a temperature range from 0° C. to +60° C., preferably at +20° C. to +40° C. The reactions can take place under normal, under elevated or under reduced pressure (e.g. from 0.5 to 5 bar). They are generally carried out under atmospheric pressure.

The compounds of the formula (I) may also result directly in the form of their salts in the preparation by the processes described above. These salts can be converted where appropriate by treatment with a base or acid in an inert solvent, by chromatographic methods or by ion exchange resins, into the respective free bases or acids. Further salts of the compounds according to the invention can also be prepared where appropriate by exchange of counterions by means of ion exchange chromatography, for example with Amberlite® resins.

Functional groups which are present where appropriate in the radicals $R^4$, $R^6$, $L^3$ and/or $L^4$—such as, in particular, amino, guanidine, hydroxy, mercapto and carboxyl groups—may, if expedient or necessary, also be in temporarily protected form in the reaction sequences described above. The introduction and removal of such protective groups takes place in this connection by conventional methods known from peptide chemistry [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984].

The amino and guanidine protective group which is preferably used is tert-butoxycarbonyl (Boc) or benzyloxycarbonyl (Z). The protective group preferably employed for a hydroxy or carboxyl function is preferably tert-butyl or benzyl. Elimination of these protective groups is carried out by conventional methods, preferably by reaction with a strong acid such as hydrogen chloride, hydrogen bromide or trifluoroacetic acid in an inert solvent such as dioxane, dichloromethane or acetic acid; the elimination can where appropriate also take place without an additional inert solvent. In the case of benzyl and benzyloxycarbonyl as protective group, these can also be removed by hydrogenolysis in the presence of a palladium catalyst. Elimination of the protective groups mentioned may where appropriate be carried out simultaneously in a one-pot reaction or in separate reaction steps.

The compounds of the formulae (II), (III), (IV), (VIII), (IX), (X), (XI), (XII) and (XIII) are commercially available, known from the literature or can be prepared by methods customary in the literature. Thus, for example, compounds of the formulae (II) and (VIII) in which $L^1$ or $L^2$ is —$CH_2$— can be obtained by known methods for chain extension of carboxylic acids, such as, for example, the Arndt-Eistert reactions [Eistert et al., *Ber. Dtsch. Chem. Ges.* 60, 1364-1370 (1927); Ye et al., *Chem. Rev.* 94, 1091-1160 (1994); Cesar et al., *Tetrahedron Lett.* 42, 7099-7102 (2001)] or the reaction with N-hydroxy-2-thiopyridone [cf. Barton et al., *Tetrahedron Lett.* 32, 3309-3312 (1991)], starting from the corresponding compounds in which $L^1$ or $L^2$ is a bond.

Preparation of compound (A), 2-amino-6-({[2-(4-chlorophenyl)-1,3-thiazol-4-yl]methyl}thio)-4-[4-(2-hydroxyethoxy)phenyl]pyridine-3,5-dicarbonitrile, is described in WO 03/053441 as example 6.

The preparation of the compounds according to the invention can be illustrated by the following synthesis schemes:

Scheme 1

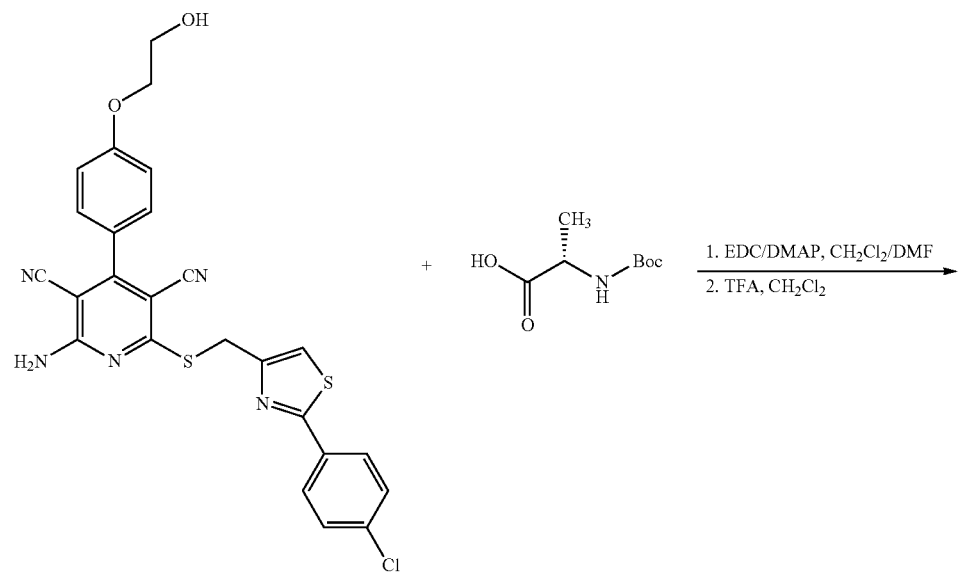

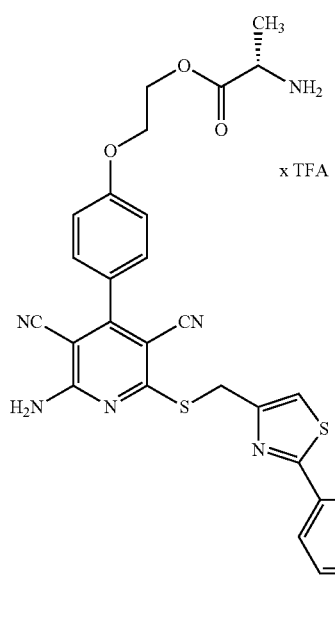
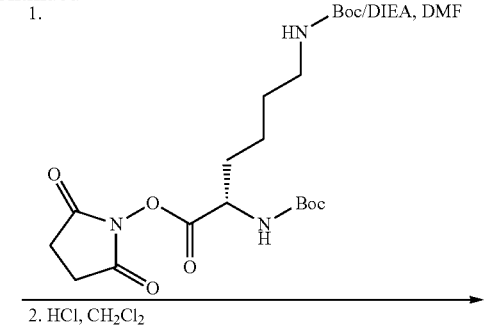
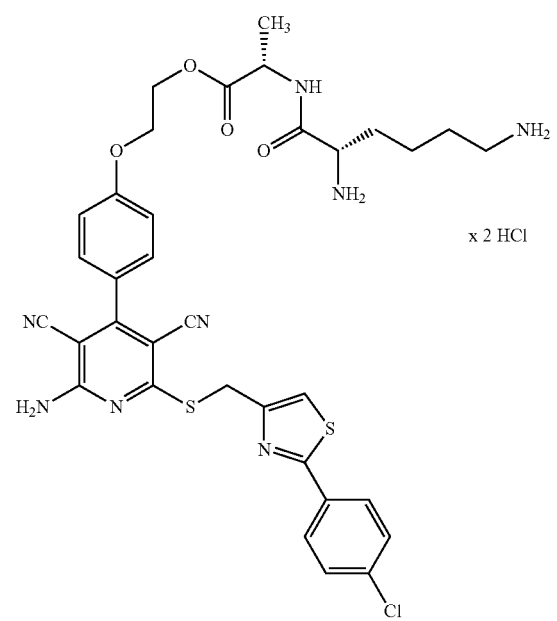

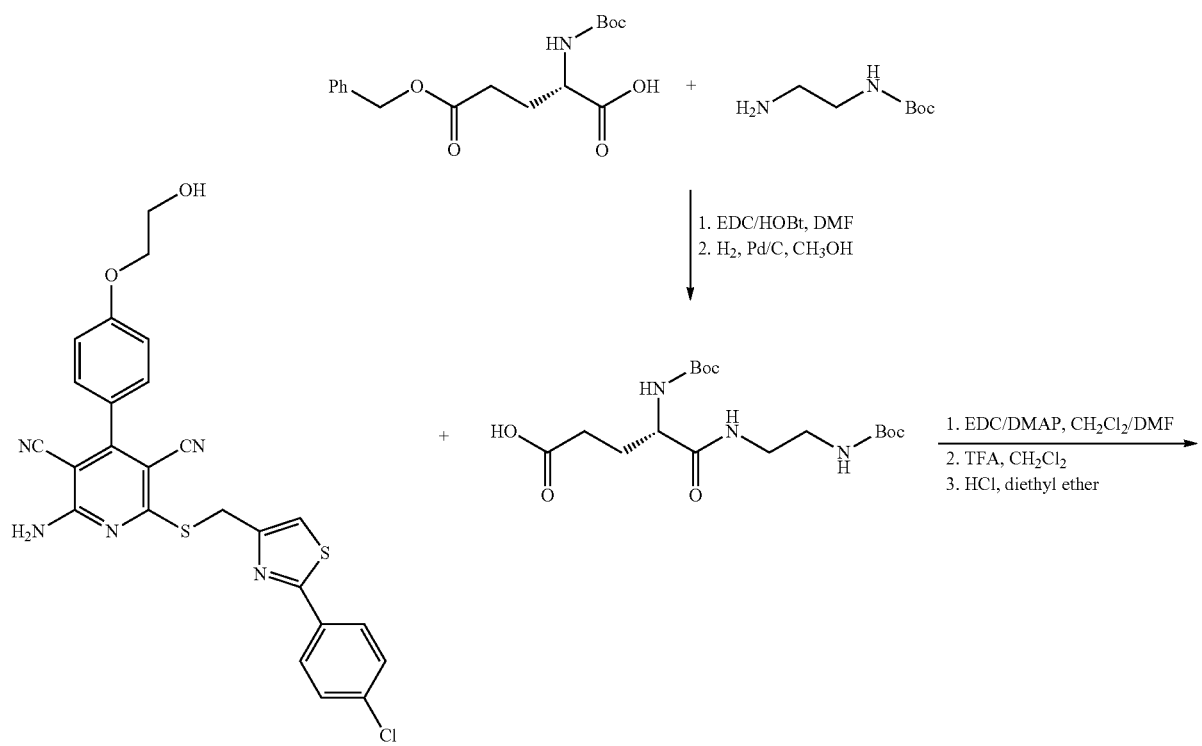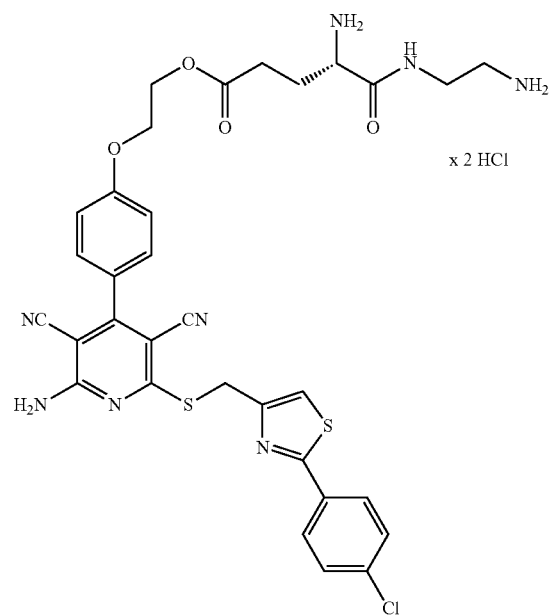

Scheme 3
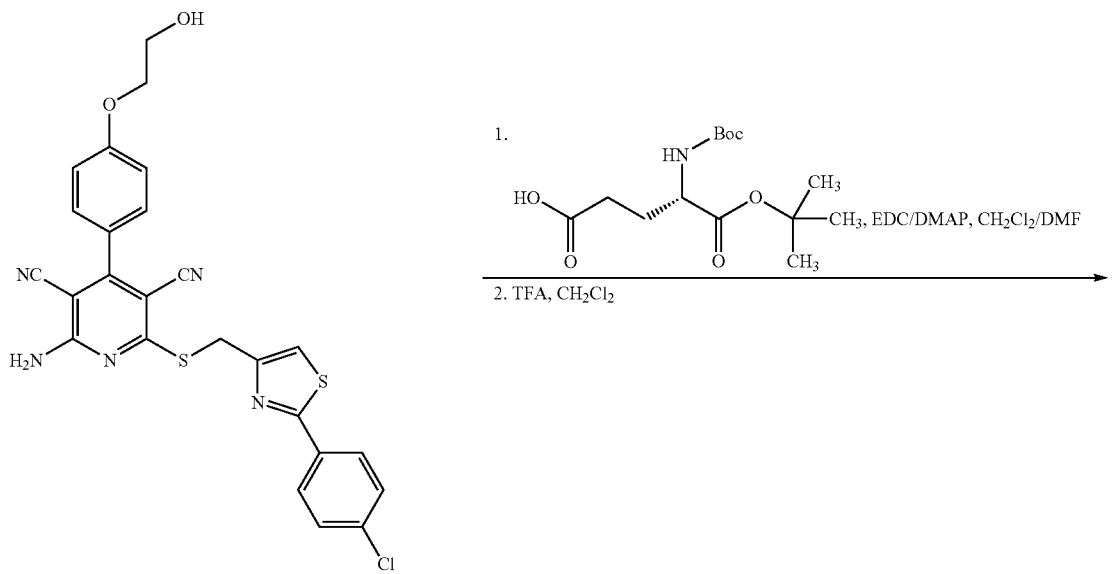
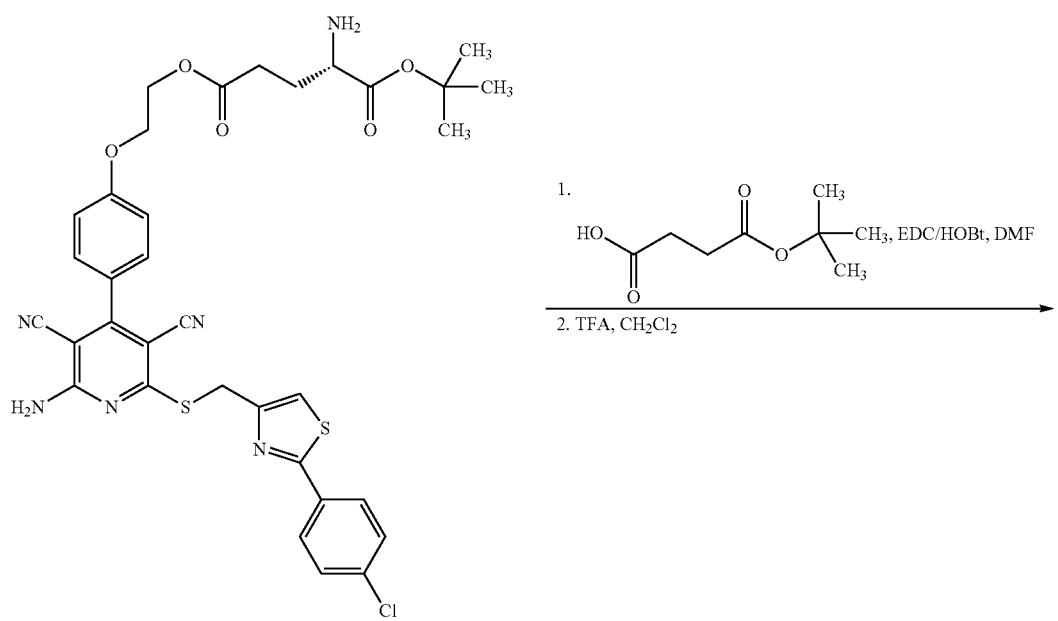

-continued

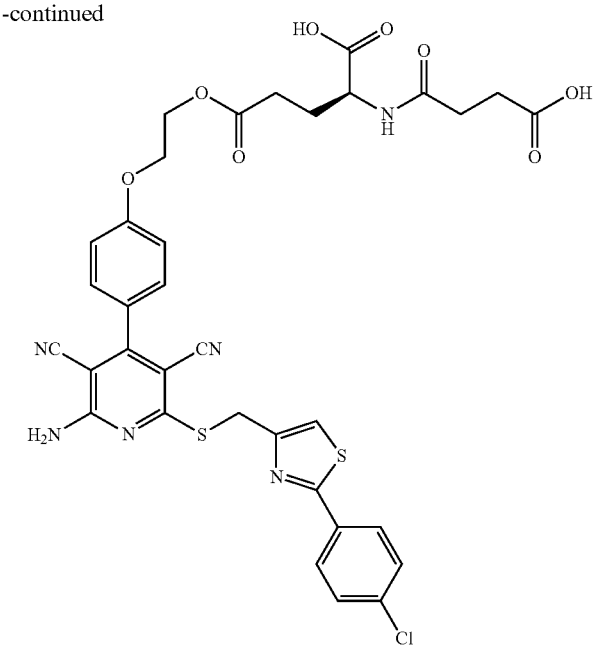

The compounds according to the invention and their salts represent useful prodrugs of the active ingredient compound (A). On the one hand, they show good stability at various pH values and, on the other hand, they show efficient conversion into the active ingredient compound (A) at a physiological pH and in particular in vivo. The compounds according to the invention moreover have improved solubilities in aqueous or other physiologically tolerated media, making them suitable for therapeutic use, in particular on intravenous administration. In addition, the bioavailability from suspension after oral administration is improved by comparison with the parent substance (A).

The compounds of the formula (I) are suitable alone or in combination with one or more other active ingredients for the prophylaxis and/or treatment of various disorders, for example and in particular disorders of the cardiovascular system (cardiovascular disorders), for cardio protection following lesions of the heart, and of metabolic disorders.

Disorders of the cardiovascular system, or cardiovascular disorders, mean in the context of the present invention for example the following disorders: hypertension (high blood pressure), peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, princemetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially hypertension, coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further also suitable in particular for reducing the area of myocardium affected by an infarction, and for the prophylaxis of secondary infarctions.

The compounds according to the invention are furthermore suitable in particular for the prophylaxis and/or treatment of thromboembolic disorders, reperfusion damage following ischemia, micro- and macromuscular lesions (vasculitis), arterial and venous thromboses, edemas, ischemias such as myocardial infarction, stroke and transient ischemic attacks, for cardio protection in connection with coronary artery bypass operations (CABG), primary percutaneous transluminal coronary angioplasties (PTCAs), PTCAs after thrombolysis, rescue PTCA, heart transplants and open-heart operations, and for organ protection in connection with transplants, bypass operations, catheter investigations and other surgical procedures.

Further indication areas for which the compounds according to the invention can be used are for example the prophylaxis and/or treatment of disorders of the urogenital region, such as, for example, acute renal failure, unstable bladder, urogenital incontinence, erectile dysfunction and female sexual dysfunction, but also the prophylaxis and/or treatment of inflammatory disorders such as, for example, inflammatory dermatoses and arthritis, especially rheumatoid arthritis, of disorders of the central nervous system and neurodegenerative impairments (post-stroke conditions, Alzheimer's disease, Parkinson's disease, dementia, Huntington's chorea, epilepsy, depression, multiple sclerosis), of painful conditions and migraine, hepatic fibrosis and cirrhosis of the liver, of cancers and of nausea and vomiting in connection with cancer therapies, and for wound healing.

A further indication area is for example the prophylaxis and/or treatment of respiratory disorders such as, for example, asthma, chronic obstructive respiratory disorders (COPD, chronic bronchitis), pulmonary emphysema, bronchiectasies, cystic fibrosis (mucoviscidosis) and pulmonary hypertension, especially pulmonary aterial hypertension.

Finally, the compounds according to the invention are also suitable for the prophylaxis and/or treatment of metabolic disorders such as, for example, diabetes, especially diabetes mellitus, gestational diabetes, insulin-dependent diabetes and non-insulin-dependent diabetes, diabetic sequelae such as, for example, retinopathy, nephropathy and neuropathy, metabolic disorders such as, for example, metabolic syndrome, hyperglycemia, hyperinsulinemia, insulin resistance, glucose intolerance and obesity (adiposity), and arteriosclerosis and dyslipidemias (hypercholesterolemia, hypertriglyceridemia, elevated concentrations of post-prandial plasma triglycerides, hypoalphalipoproteinemia, combined hyperlipidemias), especially, of diabetes, metabolic syndrome and dyslipidemias.

The present invention further relates to the use of the compounds according to the invention for the treatment and/or prophylaxis of disorders, especially of the aforementioned disorders.

The present invention further relates to the use of the compounds according to the invention for the manufacture of a medicament for the treatment and/or prophylaxis of disorders, especially of the aforementioned disorders.

The present invention further relates to a method for the treatment and/or prophylaxis of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one of the compounds according to the invention and one or more further active ingredients, in particular for the treatment and/or prophylaxis of the aforementioned disorders.

Suitable combination active ingredients which may be mentioned by way of example and preferably are: lipid metabolism-altering active ingredients, antidiabetics, blood pressure-reducing agents, agents which promote blood flow and/or have antithrombotic effects, antiarrhythmics, antioxidants, chemokine receptor antagonists, p38 kinase inhibitors, NPY agonists, orexin agonists, anorectic agents, PAF-AH inhibitors, anti-inflammatory agents (COX inhibitors, LTB$_4$ receptor antagonists), and analgesics such as, for example, aspirin.

The present invention relates in particular to combinations of at least one of the compounds according to the invention with at least one lipid metabolism-altering active ingredient, antidiabetic, blood pressure reducing active ingredient, antiarrhythmic and/or agent having antithrombotic effects.

The compounds according to the invention can preferably be combined with one or more lipid metabolism-altering active ingredients, by way of example and preferably from the group of HMG-CoA reductase inhibitors, inhibitors of HMG-CoA reductase expression, squalene synthesis inhibitors, ACAT inhibitors, LDL receptor inducers, cholesterol absorption inhibitors, polymeric bile acid adsorbents, bile acid reabsorption inhibitors, MTP inhibitors, lipase inhibitors, LPL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP-citrate lyase inhibitors, Lp(a) antagonists, cannabinoid receptor 1 antagonists, leptin receptor agonists, bombesin receptor agonists, histamine receptor agonists, and of antioxidants/radical scavengers;

antidiabetics which are mentioned in the Rote Liste 2004/II, Chapter 12, and, by way of example and preferably, those from the group of sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of hepatic enzymes involved in the stimulation of gluconeogenesis and/or glycogenolysis, modulators of glucose uptake, and of potassium channel openers such as, for example, those disclosed in WO 97/26265 and WO 99/03861;

blood pressure-reducing active ingredients, by way of example and preferably from the group of calcium antagonists, angiotensin AII antagonists, ACE inhibitors, rennin inhibitors, beta-adrenoceptor antagonists, alpha-adrenoceptor antagonists, diuretics, aldosterone antagonists, mineralocorticoid receptor antagonists, ECE inhibitors, and of vasopeptidase inhibitors;

agents having antithrombotic effects, by way of example and preferably from the group of platelet aggregation inhibitors or of anticoagulants;

antiarrhythmics, especially those for the treatment of supraventricular arrhythmias and tachycardias;

substances for the prophylaxis and treatment of ischemic and reperfusion damage;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

agonists of the prostacyclin receptor (IP receptor), such as, for example iloprost, beraprost and cicaprost;

calcium sensitizers such as by way of example and preferably levosimendan;

potassium supplements;

NO and heme-independent activators of guanylate cyclase, such as in particular the compounds described in WO 01/19355, WO 01/19776, WO 01/19778, WO 01/19780, WO 02/070462 and WO 02/070510;

NO-independent but heme-dependent stimulators of guanylate cyclase, such as in particular the compounds described in WO 00/06568, WO 00/06569, WO 02/42301 and WO 03/095451;

Inhibitors of human neutrophil elastase (HNE), such as, for example, sivelestat and DX-890 (reltran);

compounds which inhibit the signal transduction cascade, such as, for example, tyrosine kinase inhibitors, especially sorafenib, imatinib, gefitinib and erlotinib;

compounds which influence the energy metabolism of the heart, such as, for example, etomoxir, dichloroacetate, ranolazine and trimetazidine;

analgesics; and/or substances for the prophylaxis and treatment of nausea and vomiting Lipid metabolism-altering active ingredients preferably mean compounds from the group of HMG-CoA reductase inhibitors, squalene synthesis inhibitors, ACAT inhibitors, choleseterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbents, bile acid reabsorption inhibitors, antioxidants/radical scavengers, and cannabinoid receptor 1 antagonists.

In a preferred embodiment of the invention, the compounds according to the invention are administered in combination with an HMG-CoA reductase inhibitor from the class of statins, such as by way of example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as by way of example and preferably BMS-188494 or TAK-475.

In a preferred embodiment of the invention, the compounds according to the invention are administered in combination with an ACAT inhibitor, such as by way of example and preferably avasimibe, melinamide, pactimibe, eflucimibe or SMP-797.

In a preferred embodiment of the invention, the compounds according to the invention are administered in combination with a cholesterol absorption inhibitor, such as by way of example and preferably ezetimibe, tiqueside or pamaqueside.

In a preferred embodiment of the invention, the compounds according to the invention are administered in combination with an MTP inhibitor, such as by way of example and preferably implitapide, BMS-201038, R-103757 or JTT-130.

In a preferred embodiment of the invention, the compounds according to the invention are administered in combination with a lipase inhibitor, such as by way of example and preferably orlistat.

In a preferred embodiment of the invention, the compounds according to the invention are administered in combination with a thyroid hormone and/or thyroid mimetic, such as by way of example and preferably D-thyroxine or 3,5,3'-triiodothyronine (T3).

In a preferred embodiment of the invention, the compounds according to the invention are administered in combination with an agonist of the niacin receptor, such as by way of example and preferably niacin, acipimox, acifran or radecol.

In a preferred embodiment of the invention, the compounds according to the invention are administered in combination with a CETP inhibitor, such as by way of example and preferably torcetrapib, JTT-705, BAY 60-5521, BAY 78-7499 or CETP vaccine (Avant).

In a preferred embodiment of the invention, the compounds according to the invention are administered in combination with a PPAR-γ agonist, such as by way of example and preferably pioglitazone or rosiglitazone.

In a preferred embodiment of the invention, the compounds according to the invention are administered in combination with a PPAR-δ agonist, such as by way of example and preferably GW-501516 or BAY 68-5042.

In a preferred embodiment of the invention, the compounds according to the invention are administered in combination with a polymeric bile acid adsorbent, such as by way of example and preferably cholestyramine, colestipol, colesolvam, CholestaGel or colestimide.

In a preferred embodiment of the invention, the compounds according to the invention are administered in combination with a bile acid reabsorption inhibitor, such as by way of example and preferably ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as by way of example and preferably probucol, AGI-1067, BO-653 or AEOL-10150.

In a preferred embodiment of the invention, the compounds according to the invention are administered in combination with a cannabinoid receptor 1 antagonist, such as by way of example and preferably rimonabant or SR-147778.

Antidiabetics preferably mean insulin and insulin derivatives, and orally active hypoglycemic active ingredients. Insulin and insulin derivatives includes in this connection both insulins of animal, human or biotechnological origin and mixtures thereof. The orally active hypoglycemic active ingredients preferably include sulfonylureas, biguanides, meglitinide derivatives, glucosidase inhibitors, DPP-IV inhibitors and PPAR-γ agonists.

In a preferred embodiment of the invention, the compounds according to the invention are administered in combination with insulin.

In a preferred embodiment of the invention, the compounds according to the invention are administered in combination with a sulfonylurea, such as by way of example and preferably tolbutamide, glibenclamide, glimepiride, glipizide or gliclazide.

In a preferred embodiment of the invention, the compounds according to the invention are administered in combination with a biguanide, such as by way of example and preferably metformin.

In a preferred embodiment of the invention, the compounds according to the invention are administered in combination with a meglitinide derivative, such as by way of example and preferably repaglinide or nateglinide.

In a preferred embodiment of the invention, the compounds according to the invention are administered in combination with a glucosidase inhibitor, such as by way of example and preferably miglitol or acarbose.

In a preferred embodiment of the invention, the compounds according to the invention are administered in combination with a DPP-IV inhibitor, such as by way of example and preferably sitagliptin or vildagliptini.

In a preferred embodiment of the invention, the compounds according to the invention are administered in combination with a PPAR-γ agonist, for example from the class of thiazolidinediones, such as by way of example and preferably pioglitazone or rosiglitazone.

Blood pressure-reducing agents preferably mean compounds from the group of calcium antagonists, angiotensin AII antagonists, ACE inhibitors, renin inhibitors, beta-adrenoceptor antagonists, alpha-adrenoceptor antagonists and diuretics.

In a preferred embodiment of the invention, the compounds according to the invention are administered in combination with a calcium antagonist, such as by way of example and preferably nifedipine, amlodipine, verapamil or diltiazem.

In a preferred embodiment of the invention, the compounds according to the invention are administered in combination with an angiotensin AII antagonist, such as by way of example and preferably losartan, valsartan, candesartan, embusartan, olmesartan or telmisartan.

In a preferred embodiment of the invention, the compounds according to the invention are administered in combination with an ACE inhibitor, such as by way of example and preferably enalapril, captopril, lisinopril, ramipril, delapril, fosinopril, quinopril, perindopril or trandopril.

In a preferred embodiment of the invention, the compounds according to the invention are administered in combination with a renin inhibitor, such as by way of example and preferably aliskiren, SPP-600 or SPP-800.

In a preferred embodiment of the invention, the compounds according to the invention are administered in combination with a beta-adrenoceptor antagonist, such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-adrenoceptor antagonist, such as by way of example and preferably prazosin.

In a preferred embodiment of the invention, the compounds according to the invention are administered in combination with a diuretic, such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

In a preferred embodiment of the invention, the compounds according to the invention are administered in combination with an aldosterone or mineralocorticoid receptor antagonist, such as by way of example and preferably spironolactone or eplerenone.

In a preferred embodiment of the invention, the compounds according to the invention are administered in combination with a vasopressin receptor antagonist, such as by way of example and preferably conivaptan, tolvaptan, lixivaptan or SR-121463.

In a preferred embodiment of the invention, the compounds according to the invention are administered in combination with an organic nitrate or NO donor, such as by way of example and preferably sodium nitroprusside, glycerol nitrate, isosorbide mononitrate, isosorbide dinitrate, molsidomine or SIN-1, or in combination with inhaled NO.

In a preferred embodiment of the invention, the compounds according to the invention are administered in combination with a compound having positive inotropic activity, such as by way of example and preferably cardiac glycosides (digoxin) and beta-adrenergic and dopaminergic agonists such as isoproterenol, adrenaline, noradrenaline, dopamine or dobutamine.

In a preferred embodiment of the invention, the compounds according to the invention are administered in combination with antisympathotonics such as reserpine, clonidine or alpha-methyldopa, or in combination with potassium channel agonists such as minoxidil, diazoxide, dihydralazine or hydralazine.

Agents having an antithrombotic effect preferably mean compounds from the group of platelet aggregation inhibitors or of anticoagulants.

In a preferred embodiment of the invention, the compounds according to the invention are administered in combination with a platelet aggregation inhibitor, such as by way of example and preferably aspirin, clopidogrel, ticlopidine or dipyridamole.

In a preferred embodiment of the invention, the compounds according to the invention are administered in combination with a thrombin inhibitor, such as by way of example and preferably ximelagatran, melagatran, bivalirudin or clexane.

In a preferred embodiment of the invention, the compounds according to the invention are administered in combination with a GPIIb/IIIa antagonist, such as by way of example and preferably tirofiban or abciximab.

In a preferred embodiment of the invention, the compounds according to the invention are administered in combination with a factor Xa inhibitor, such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as by way of example and preferably coumarin.

Antiarrhythmics preferably means substances from the group of class Ia antiarrhythmics (e.g. quinidine), of class Ic antiarrhythmics (e.g. flecainide, propafenone), of class II antiarrhythmics (e.g. metoprolol, atenolol, sotalol, oxprenolol and other beta-receptor blockers), of class III antiarrhythmics (e.g. sotalol, amiodarone) and of class IV antiarrhythmics (e.g. digoxin, and verapamil, diltiazem and other calcium antagonists).

Particular preference is given in the context of the present invention to combinations comprising at least one of the compounds according to the invention and one or more further active ingredients selected from the group consisting of HMG-CoA reductase inhibitors (statins), diuretics, beta-adrenoceptor antagonists, alpha-adrenoceptor antagonists, organic nitrates and NO donors, calcium antagonists, ACE inhibitors, angiotensin AII antagonists, aldosterone and mineralocorticoid receptor antagonists, vasopressin receptor antagonists, platelet aggregation inhibitors, anticoagulants and antiarrhythmics, and to the use thereof for the treatment and/or prophylaxis of the aforementioned disorders.

The present invention further relates to medicaments which comprise at least one compound according to the invention, normally together with one or more inert, non-toxic, pharmaceutically suitable excipients, and to the use thereof for the aforementioned purposes.

The compounds according to the invention can act systemically and/or locally. For this purpose, they can be administered in a suitable way such as, for example, by the oral, parenteral, pulmonary, nasal, sublingual, lingual, buccal, rectal, dermal, transdermal, conjunctival or otic route or as an implant or stent. The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays, tablets for lingual, sublingual or buccal administration, films/wafers or capsules, suppositories, preparations for the eyes or ears, vaginal capsules, aqueous suspensions (lotions, shaking mixtures), lipophilic suspensions, ointments, creams, transdermal therapeutic systems (such as, for example, patches), milk, pastes, foams, dusting powders, implants or stents.

Oral or parenteral administration is preferred, especially oral and intravenous administration.

The compounds according to the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxy-sorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and masking flavors and/or odors.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

Abbreviations and Acronyms

Boc Tert-Butoxycarbonyl
DIEA N,N-Diisopropylethylamine
DMAP 4-N,N-Dimethylaminopyridine
DMF N,N-Dimethylformamide
DMSO Dimethyl sulfoxide
EDC 1-(3-Dimethylaminopropyl)-3-ethylcarbodiimide hydrochloride
ESI Electrospray ionization (in MS)
h Hour(s)
HOBt 1-Hydroxybenzotriazole
HPLC High pressure, high performance liquid chromatography
LC-MS Coupled liquid chromatography-mass spectrometry
min Minute(s)
MS Mass spectrometry
NMR Nuclear magnetic resonance spectrometry
p para
Pd/C Palladium on activated carbon
Ph Phenyl
quant. quantitative (for yield)
RT Room temperature
$R_t$ Retention time (in HPLC)
tert. Tertiary
TFA Trifluoroacetic acid
THF Tetrahydrofuran
UV Ultraviolet spectrometry
v/v Volume to volume ratio (of a solution)
Z Benzyloxycarbonyl LC-MS and HPLC Methods:

Method 1 (LC-MS):

MS instrument type: Micromass ZQ; HPLC instrument type: Waters Alliance 2795; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 2 (LC-MS):

Instrument: Micromass Quattro LCZ with HPLC Agilent Series 1100; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 3 (LC-MS):

MS instrument type: Micromass ZQ; HPLC instrument type: HP 1100 Series; UV DAD; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS):

MS instrument type: Micromass ZQ; HPLC instrument type: HP 1100 Series; UV DAD; column: Phenomenex Gemini 3μ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 5 (Preparative HPLC):
HPLC instrument type: Abimed/Gilson Pump 305/306; Manometric Module 806; UV Knauer Variable Wavelength Monitor; column: Gromsil C18, 10 nm, 250 mm×30 mm; eluent A: 1 l water+0.5 ml 99% trifluoroacetic acid, eluent B: 1 acetonitrile; gradient: 0.0 min 2% B→10 min 2% B→50 min 90% B; flow rate: 20 ml/min; volume: 628 ml A and 372 ml B.

Method 6a (Preparative HPLC):
Column: VP 250/21 Nukleodur 100-5 C18 ec, Macherey & Nagel Nr. 762002; eluent A: water/0.01% trifluoroacetic acid, eluent B: acetonitrile/0.01% trifluoroacetic acid; gradient: 0 min 0% B→20 min 20% B→40 min 20% B→60 min 30% B→80 min 30% B→90 min 100% B→132 min 100% B; flow rate: 5 ml/min; temperature: RT; UV detection: 210 nm.

Method 6b (Preparative HPLC):
Column: VP 250/21 Nukleodur 100-5 C18 ec, Macherey & Nagel Nr. 762002; eluent A: 1 liter water/1 ml 99% trifluoroacetic acid, eluent B: 1 liter acetonitrile/1 ml 99% trifluoroacetic acid; gradient: 0 min 30% B→20 min 50% B→40 min 80% B→60 min 100% B; flow rate: 5 ml/min; temperature: RT; UV detection: 210 nm.

Method 7 (Analytical HPLC):
Column: XTerra 3.9×150 WAT 186000478; eluent A: 10 ml 70% perchloric acid in 2.5 liters water, eluent B: acetonitrile; gradient: 0.0 min 20% B→1 min 20% B→4 min 90% B→9 min 90% B; temperature: RT; flow rate: 1 ml/min.

Method 8 (LC-MS):
Instrument: Micromass Quattro LCZ with HPLC Agilent Series 1100; column: Phenomenex Onyx Monolithic C18, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow rate: 2 ml/min; oven: 40° C.; UV detection: 208-400 nm.

Method 9 (LC-MS):
Instrument: Micromass Platform LCZ with HPLC Agilent Series 1100; column: Thermo Hypersil GOLD 3μ, 20 mm×4 mm; eluent A: 1 l water+0.5 ml 50% formic acid, eluent B: 1 l acetonitrile+0.5 ml 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 10 (LC-MS):
MS instrument type: Micromass ZQ; HPLC instrument type: HP 1100 Series; UV DAD; column: Phenomenex Gemini 3μ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 11 (LC-MS):
MS instrument type: Micromass ZQ; HPLC instrument type: Waters Alliance 2795; column: Phenomenex Synergi 2.5μ MAX-RP 100A Mercury 20 mm×4 mm; eluent A: 1 l water+0.5 ml 50% formic acid, eluent B: 1 l acetonitrile+0.5 ml 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 12 (LC-MS):
Instrument: Micromass Quattro LCZ with HPLC Agilent Series 1100; column: Phenomenex Synergi 2.5μ MAX-RP 100A Mercury 20 mm×4 mm; eluent A: 1 l water+0.5 ml 50% formic acid, eluent B: 1 l acetonitrile+0.5 ml 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 13 (LC-MS):
Instrument: Micromass QuattroPremier with Waters HPLC Acquity; column: Thermo Hypersil GOLD 1.9μ, 50 mm×1 mm; eluent A: 1 l water+0.5 ml 50% formic acid, eluent B: 1 l acetonitrile+0.5 ml 50% formic acid; gradient: 0.0 min 100% A→0.1 min 100% A→1.5 min 10% A→2.2 min 10% A; oven: 50° C.; flow rate: 0.33 ml/min; UV detection: 210 nm.

Starting Compounds and Intermediates

Example 1A

2-{4-[2-Amino-6-({[2-(4-chlorophenyl)-1,3-thiazol-4-yl]methyl}thio)-3,5-dicyanopyridin-4-yl]phenoxy}ethyl L-valinate trifluoroacetate

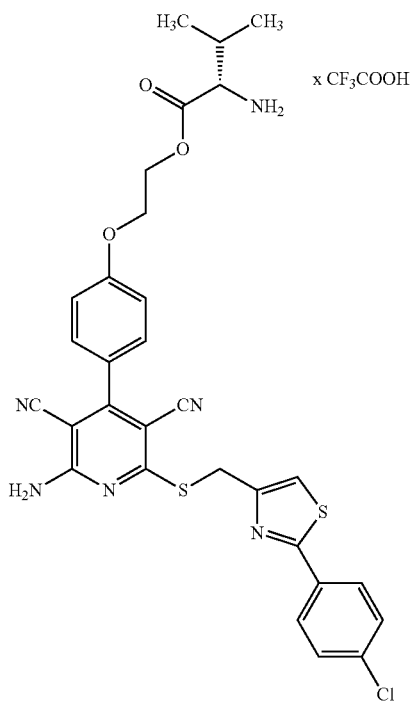 [SMILES: CC(C)[C@H](N)C(=O)OCCOc1ccc(-c2c(C#N)c(N)nc(SCc3csc(-c4ccc(Cl)cc4)n3)c2C#N)cc1]

1 g (1.92 mmol) of 2-amino-6-({[2-(4-chlorophenyl)-1,3-thiazol-4-yl]methyl}thio)-4-[4-(2-hydroxy-ethoxy)phenyl]pyridine-3,5-dicarbonitrile [WO 03/053441, example 6], 0.460 g (2.11 mmol) of N-Boc-L-valine, 0.442 g (2.31 mmol) of 1-(3-dimethylaminopropyl)-3-ethylcarbodiimide hydrochloride and 0.023 g (0.19 mmol) of 4-dimethylaminopyridine are mixed in 40 ml of dichloromethane and 10 ml of DMF and stirred at room temperature overnight. A clear solution results. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is purified by flash chromatography on silica gel with dichloromethane/ethyl acetate as eluent (gradient 10:1→7:1→5:1). The appropriate fractions are combined and the solvent is removed in vacuo. After the residue has been dried under high vacuum, 0.85 g (62% of theory) of the Boc-protected intermediate remains.

The residue is taken up in 5 ml of dichloromethane and 5 ml of anhydrous trifluoroacetic acid, and the solution is stirred at room temperature for 2 h. The mixture is then concentrated to dryness, and the residue is stirred with ethyl acetate. The precipitate which separates out is filtered off, washed with diethyl ether and then dried under high vacuum. 935 mg (quant.) of the title compound result as colorless crystals.

HPLC (Method 7): $R_t$=5.5 min;
LC-MS (Method 10): $R_t$=2.06 min; MS (ESIpos): m/z=619 (M+H)$^+$.

Example 2A

2-{4-[2-Amino-6-({[2-(4-chlorophenyl)-1,3-thiazol-4-yl]methyl}thio)-3,5-dicyanopyridin-4-yl]-phenoxy}ethyl L-alaninate trifluoroacetate

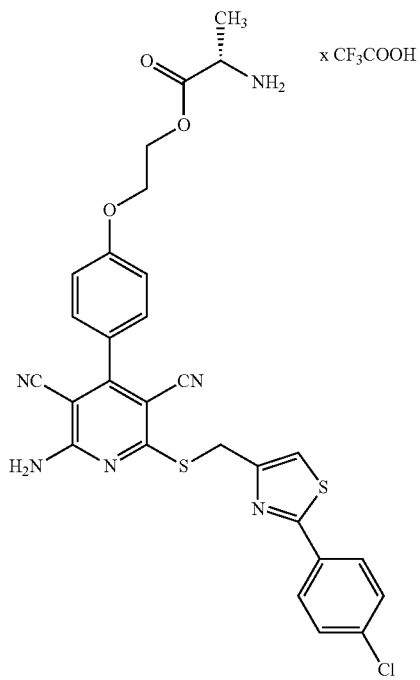 [SMILES: C[C@H](N)C(=O)OCCOc1ccc(-c2c(C#N)c(N)nc(SCc3csc(-c4ccc(Cl)cc4)n3)c2C#N)cc1]

1.5 g (2.88 mmol) of 2-amino-6-({[2-(4-chlorophenyl)-1,3-thiazol-4-yl]methyl}thio)-4-[4-(2-hydroxyethoxy)phenyl] pyridine-3,5-dicarbonitrile, 1.64 g (8.66 mmol) of N-Boc-L-alanine, 0.719 g (3.75 mmol) of 1-(3-dimethylaminopropyl)-3-ethylcarbodiimide hydrochloride and 0.176 g (1.44 mmol) of 4-dimethylaminopyridine are mixed in 25 ml of dichloromethane and 25 ml of DMF and stirred at room temperature for 2 h. The mixture is then concentrated in vacuo and the residue is taken up in ethyl acetate. The solution is extracted twice with 5% strength citric acid and twice with sodium bicarbonate solution. The organic phase is concentrated and the residue is stirred with 50 ml of diethyl ether and 50 ml of pentane. The precipitate is filtered off with suction and washed with pentane. After the residue has been dried under high vacuum, 1.23 g (62% of theory) of the Boc-protected intermediate remain.

The residue is taken up in 18 ml of dichloromethane and 2 ml of anhydrous trifluoroacetic acid, and the solution is treated in an ultrasonic bath at room temperature for 1 h. The mixture is then concentrated to dryness, and the remaining residue is stirred with diethyl ether. The precipitate which separates out is filtered off, washed with diethyl ether and then dried under high vacuum. 1200 mg (96% of theory) of the title compound result as colorless crystals.

HPLC (Method 7): $R_t$=5.3 min;
LC-MS (Method 12): $R_t$=1.73 min; MS (ESIpos): m/z=591 (M+H)$^+$.

Example 3A

2-{4-[2-Amino-6-({[2-(4-chlorophenyl)-1,3-thiazol-4-yl]methyl}thio)-3,5-dicyanopyridin-4-yl]-phenoxy}ethyl O-tert-butyl-L-serinate

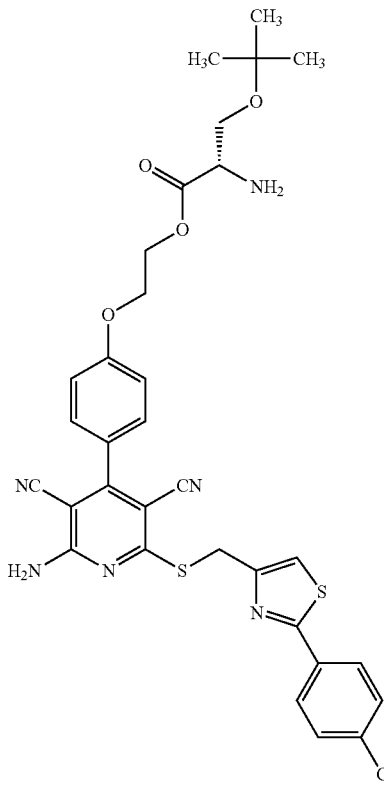

1 g (1.92 mmol) of 2-amino-6-({[2-(4-chlorophenyl)-1,3-thiazol-4-yl]methyl}thio)-4-[4-(2-hydroxy-ethoxy)phenyl] pyridine-3,5-dicarbonitrile, 0.612 g (2.12 mmol) of N-(tert-butoxycarbonyl)-O-tert-L-serine, 0.442 g (2.31 mmol) of 1-(3-dimethylaminopropyl)-3-ethylcarbodiimide hydrochloride and 0.024 g (0.192 mmol) of 4-dimethylaminopyridine are mixed in 40 ml of dichloromethane and 10 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is taken up in dichloromethane and mixed with diethyl ether. The precipitate which separates out is filtered off with suction and washed with diethyl ether. After drying under high vacuum, 1.25 g (85% of theory) of the protected intermediate remain.

The residue is taken up in 100 ml of dichloromethane and 10 ml of anhydrous trifluoroacetic acid, and the solution is stirred at room temperature for 1 h. The mixture is then poured into a mixture of half-saturated sodium bicarbonate solution and dichloromethane. The organic phase is separated off, dried over magnesium sulfate, filtered and concentrated. Drying under high vacuum results in 1020 mg (95% of theory) of the title compound as a colorless powder.

HPLC (Method 7): $R_t$=5.4 min;
LC-MS (Method 11): $R_t$=1.65 min; MS (ESIpos): m/z=663 (M+H)$^+$.

Example 4A

N²-(tert.-Butoxycarbonyl)-N-{2-[(tert-butoxycarbonyl)amino]ethyl}-L-α-glutamine

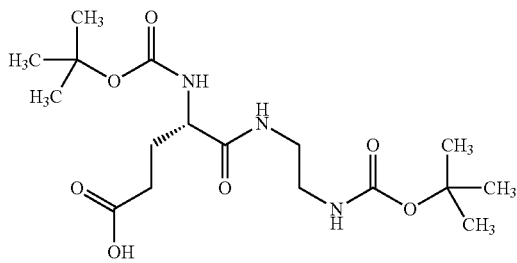 [SMILES: CC(C)(C)OC(=O)NCCNC(=O)[C@H](CCC(=O)O)NC(=O)OC(C)(C)C]

1.5 g (4.45 mmol) of (2S)-5-(benzyloxy)-2-[(tert-butoxycarbonyl)amino]-5-oxopentanoic acid, 783 mg (4.89 mmol) of tert-butyl (2-aminoethyl)carbamate, 938 mg (4.89 mmol) of 1-(3-dimethyl-aminopropyl)-3-ethylcarbodiimide hydrochloride and 749 mg (0.489 mmol) of 1-hydroxy-1H-benzotriazole hydrate are mixed in 140 ml of DMF and stirred at room temperature overnight. The mixture is then poured into a mixture of half-saturated ammonium chloride solution and ethyl acetate. The organic phase is separated off, washed successively with water, saturated sodium bicarbonate solution and saturated sodium chloride solution, dried over magnesium sulfate, filtered and concentrated. The residue is stirred with diethyl ether. The precipitate which separates out is filtered off with suction, washed with diethyl ether and dried under high vacuum. 1.9 g (89% of theory) of the protected intermediate remain.

LC-MS (Method 12): $R_t$=2.19 min; MS (ESIpos): m/z=480 (M+H)⁺.

1.9 g (3.96 mmol) of the resulting intermediate are dissolved in 125 ml of methanol and, after addition of 250 mg of 10% palladium on activated carbon, hydrogenated under atmospheric pressure at RT for 2 h. The catalyst is then filtered off, and the solvent is removed in vacuo. 1500 mg (97% of theory) of the title compound are obtained as a colorless foam.

LC-MS (Method 10): $R_t$=1.94 min; MS (ESIpos): m/z=390 (M+H)⁺.

Example 5A

N²-(tert-Butoxycarbonyl)-N-{2-[(tert-butoxycarbonyl)amino]ethyl}-L-glutamine

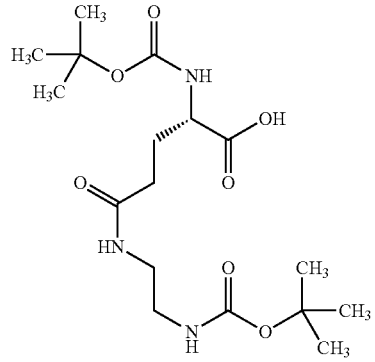 [SMILES: CC(C)(C)OC(=O)NCCNC(=O)CC[C@H](NC(=O)OC(C)(C)C)C(=O)O]

1.5 g (4.45 mmol) of (4S)-5-(benzyloxy)-2-[(tert-butoxycarbonyl)amino]-5-oxopentanoic acid, 783 mg (4.89 mmol) of tert-butyl (2-aminoethyl)carbamate, 938 mg (4.89 mmol) of 1-(3-dimethyl-aminopropyl)-3-ethylcarbodiimide hydrochloride and 749 mg (0.489 mmol) of 1-hydroxy-1H-benzotriazole hydrate are mixed in 140 ml of DMF and stirred at room temperature overnight. The mixture is then poured into a mixture of half-saturated ammonium chloride solution and ethyl acetate. The organic phase is separated off, washed successively with water, saturated sodium bicarbonate solution and saturated sodium chloride solution, dried over magnesium sulfate, filtered and concentrated. The residue is stirred with diethyl ether. The precipitate which separates out is filtered off with suction, washed with diethyl ether and dried under high vacuum. 2.1 g (98% of theory) of the protected intermediate remain.

LC-MS (Method 10): $R_t$=2.47 min; MS (ESIpos): m/z=480 (M+H)⁺.

2.1 g (4.38 mmol) of the resulting intermediate are dissolved in 140 ml of methanol and, after addition of 250 mg of 10% palladium on activated carbon, hydrogenated under atmospheric pressure at RT for 2 h. The catalyst is then filtered off and the solvent is removed in vacuo. 1540 mg (90% of theory) of the title compound are obtained as a colorless foam.

LC-MS (Method 11): $R_t$=1.35 min; MS (ESIpos): m/z=390 (M+H)⁺.

Example 6A

N²-(tert-Butoxycarbonyl)-N-{2-[(tert.-butoxycarbonyl)amino]ethyl}-L-asparagine

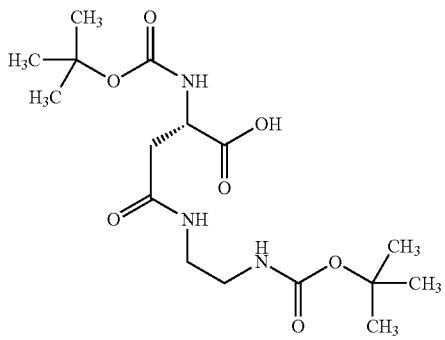 [SMILES: CC(C)(C)OC(=O)NCCNC(=O)C[C@H](NC(=O)OC(C)(C)C)C(=O)O]

1.5 g (4.64 mmol) of (3S)-4-(benzyloxy)-3-[(tert-butoxycarbonyl)amino]-4-oxobutyric acid, 818 mg (5.1 mmol) of tert-butyl-(2-aminoethyl)carbamate, 978 mg (5.1 mmol) of 1-(3-dimethylaminopropyl)-3-ethylcarbodiimide hydrochloride and 781 mg (5.1 mmol) of 1-hydroxy-1H-benzotriazole hydrate are mixed in 75 ml of DMF and stirred at room temperature overnight. The mixture is then poured into a mixture of half-saturated ammonium chloride solution and ethyl acetate. The organic phase is separated off, washed successively with water, saturated sodium bicarbonate solution and saturated sodium chloride solution, dried over magnesium sulfate, filtered and concentrated. The residue is stirred with diethyl ether. The precipitate which separates out is filtered off with suction, washed with diethyl ether and dried under high vacuum. 2.1 g (81% of theory) of the protected intermediate remain.

LC-MS (Method 10): $R_t$=2.47 min; MS (ESIpos): m/z=466 (M+H)⁺.

2.1 g (4.51 mmol) of the resulting intermediate are dissolved in 140 ml of methanol and, after addition of 250 mg of 10% palladium on activated carbon, hydrogenated under atmospheric pressure at RT for 2 h. The catalyst is then filtered off and the solvent is removed in vacuo. 1690 mg (99% of theory) of the title compound are obtained as a colorless foam.

LC-MS (Method 11): $R_t$=1.35 min; MS (ESIpos): m/z=376 (M+H)⁺.

Example 7A 5-(2-{4-[2-Amino-6-({[2-(4-chlorophenyl)-1,3-thia-zol-4-yl]methyl}thio)-3,5-dicyanopyridin-4-yl]-phenoxy}ethyl) 1-tert-butyl L-glutamate

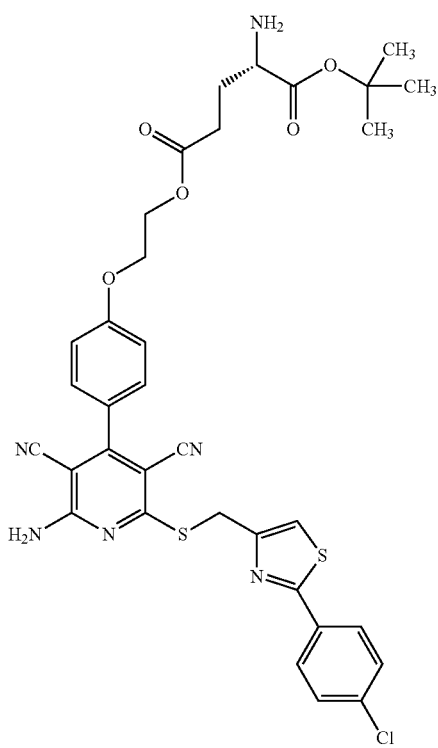 [SMILES: CC(C)(C)OC(=O)[C@@H](N)CCC(=O)OCCOc1ccc(-c2c(C#N)c(N)nc(SCc3csc(-c4ccc(Cl)cc4)n3)c2C#N)cc1]

3.117 g (6 mmol) of 2-amino-6-({[2-(4-chlorophenyl)-1,3-thiazol-4-yl]methyl}thio)-4-[4-(2-hydroxyethoxy)phenyl]pyridine-3,5-dicarbonitrile, 2 g (6.59 mmol) of (4S)-5-tert-butoxy-4-[(tert-butoxycarbonyl)amino]-5-oxopentanoate, 1.38 g (7.19 mmol) of 1-(3-dimethylaminopropyl)-3-ethyl-carbodiimide hydrochloride and 0.073 g (0.6 mmol) of 4-dimethylaminopyridine are mixed in 80 ml of dichloromethane and 20 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is precipitated from dichloromethane with petroleum ether. The product is filtered off with suction, washed with diethyl ether and dried under high vacuum. 4.44 g (92% of theory) of the protected intermediate remain.

LC-MS (Method 10): $R_t$=3.38 min; MS (ESIpos): m/z=805 (M+H)$^+$.

57 mg (0.07 mmol) of the resulting intermediate are taken up in 6 ml of dichloromethane and 0.6 ml of anhydrous trifluoroacetic acid, and the solution is stirred at room temperature for 2.5 h. The mixture is then poured into a mixture of half-saturated sodium bicarbonate solution and dichloromethane. The organic phase is separated off, dried over magnesium sulfate, filtered and concentrated. Drying under high vacuum results in 50 mg (quant.) of the title compound as a colorless powder.

HPLC (Method 7): $R_t$=5.4 min;

LC-MS (Method 11): $R_t$=1.72 min; MS (ESIpos): m/z=705 (M+H)$^+$.

Example 8A

2-{4-[2-Amino-6-({[2-(4-chlorophenyl)-1,3-thiazol-4-yl]methyl}sulfanyl)-3,5-dicyanopyridin-4-yl]-phenoxy}ethyl L-leucinate trifluoroacetate

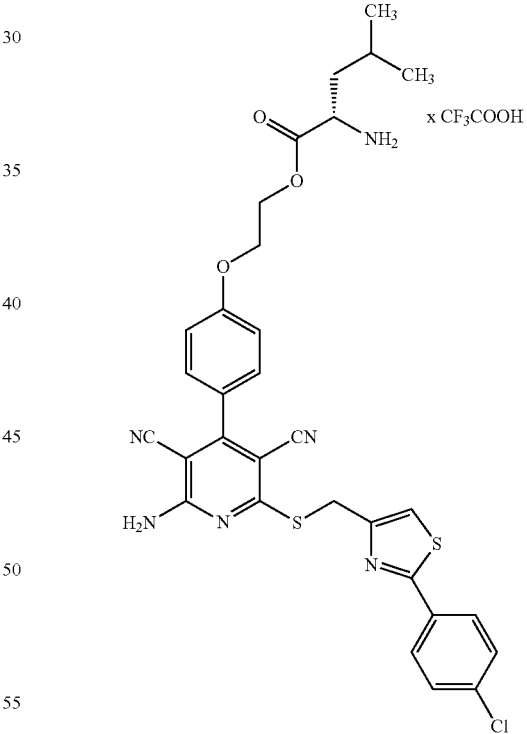

The title compound is prepared in analogy to example 1A starting from 2-amino-6-({[2-(4-chlorophenyl)-1,3-thiazol-4-yl]methyl}thio)-4-[4-(2-hydroxyethoxy)phenyl]pyridine-3,5-dicarbonitrile and Boc-L-leucine.

HPLC (Method 7): $R_t$=5.5 min;

LC-MS (Method 12): $R_t$=1.75 min; MS (ESIpos): m/z=633 (M+H)$^+$.

Example 9A

2-{4-[2-Amino-6-({[2-(4-chlorophenyl)-1,3-thiazol-4-yl]methyl}sulfanyl)-3,5-dicyanopyridin-4-yl]-phenoxy}ethyl D-alaninate trifluoroacetate

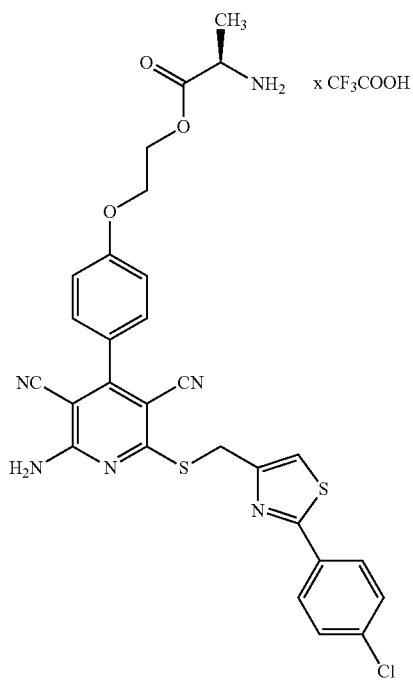 [SMILES: C[C@@H](N)C(=O)OCCOc1ccc(-c2c(C#N)c(N)nc(SCc3csc(-c4ccc(Cl)cc4)n3)c2C#N)cc1]

The title compound is prepared in analogy to example 2A starting from 2-amino-6-({[2-(4-chlorophenyl)-1,3-thiazol-4-yl]methyl}thio)-4-[4-(2-hydroxyethoxy)phenyl]pyridine-3,5-dicarbonitrile and Boc-D-alanine.

HPLC (Method 7): $R_t$=5.2 min;

LC-MS (Method 13): $R_t$=1.15 min; MS (ESIpos): m/z=591 (M+H)$^+$.

Example 10A $N^2$-(tert-Butoxycarbonyl)-N-{2-[(tert-butoxycarbonyl)amino]ethyl}-D-α-glutamine

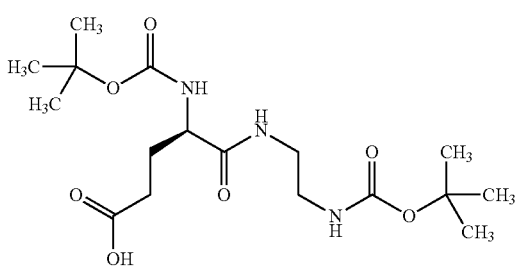 [SMILES: CC(C)(C)OC(=O)NCCNC(=O)[C@@H](CCC(=O)O)NC(=O)OC(C)(C)C]

The title compound is prepared in analogy to example 4A starting from (2R)-5-(Benzyloxy)-2-[(tert-butoxycarbonyl)amino]-5-oxopentanoic acid.

HPLC (Method 7): $R_t$=4.4 min;

LC-MS (Method 11): $R_t$=1.37 min; MS (ESIpos): m/z=390 (M+H)$^+$.

Example 11A

2-{4-[2-Amino-6-({[2-(4-chlorophenyl)-1,3-thiazol-4-yl]methyl}sulfanyl)-3,5-dicyanopyridin-4-yl]-phenoxy}ethyl glycinate trifluoroacetate

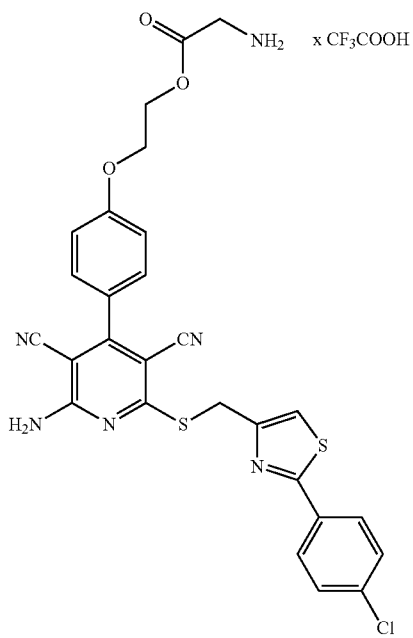 [SMILES: N#Cc1c(N)nc(SCc2csc(-c3ccc(Cl)cc3)n2)c(C#N)c1-c1ccc(OCCOC(=O)CN)cc1]

The title compound is prepared in analogy to example 2A starting from 2-amino-6-({[2-(4-chlorophenyl)-1,3-thiazol-4-yl]methyl}thio)-4-[4-(2-hydroxyethoxy)phenyl]pyridine-3,5-dicarbonitrile and Boc-glycine.

HPLC (Method 7): $R_t$=5.1 min;

LC-MS (Method 13): $R_t$=1.13 min; MS (ESIpos): m/z=577 (M+H)$^+$.

Example 12A

2-{4-[2-Amino-6-({[2-(4-chlorophenyl)-1,3-thiazol-4-yl]methyl}sulfanyl)-3,5-dicyanopyridin-4-yl]-phenoxy}ethyl L-phenylalaninate trifluoroacetate

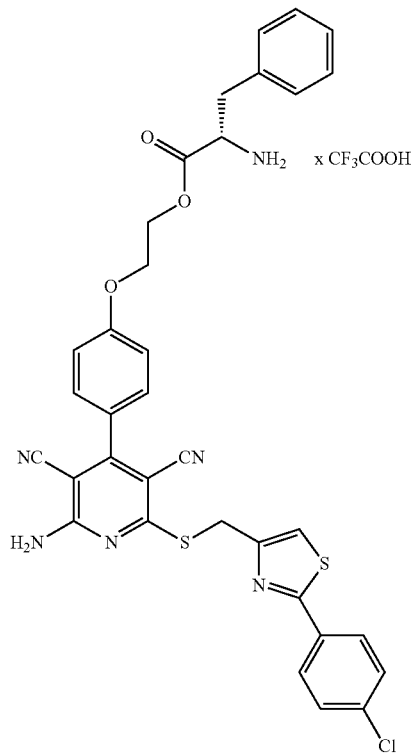 [SMILES: N#Cc1c(N)nc(SCc2csc(-c3ccc(Cl)cc3)n2)c(C#N)c1-c1ccc(OCCOC(=O)[C@@H](N)Cc2ccccc2)cc1]

The title compound is prepared in analogy to example 2A starting from 2-amino-6-({[2-(4-chlorophenyl)-1,3-thiazol-4-yl]methyl}thio)-4-[4-(2-hydroxyethoxy)phenyl]pyridine-3,5-dicarbonitrile and Boc-L-phenylalanine.

HPLC (Method 7): $R_t$=5.1 min;

LC-MS (Method 13): $R_t$=1.13 min; MS (ESIpos): m/z=577 (M+H)$^+$.

EXEMPLARY EMBODIMENTS

Example 1

2-{4-[2-Amino-6-({[2-(4-chlorophenyl)-1,3-thiazol-4-yl]methyl}thio)-3,5-dicyanopyridin-4-yl]-phenoxy}ethyl L-lysyl-L-valinate dihydrochloride

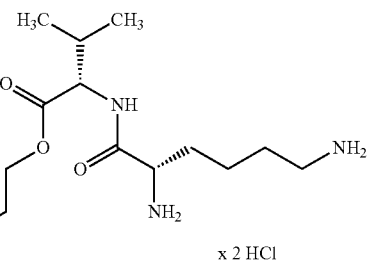

1.5 g (1.77 mmol) of the compound from example 1A, 2.36 g (5.31 mmol) of 2,5-dioxopyrrolidin-1-yl-$N^2$,$N^6$-bis(tert-butoxycarbonyl)-L-lysinate and 1.5 ml of N,N-diisopropylethylamine are mixed in 20 ml of DMF and stirred at room temperature overnight. The solvent is then removed in vacuo, and the residue is purified by flash chromatography on silica gel with dichloromethane/ethyl acetate as eluent (gradient 3:1→2:1). The appropriate fractions are combined, and the solvent is removed in vacuo. After the residue has been dried under high vacuum, 1.2 g (66% of theory) of the protected intermediate remain.

HPLC (Method 7): $R_t$=6.7 min.

1.2 g (1.27 mmol) of the resulting intermediate are taken up in 3 ml of dichloromethane and, while stirring, 50 ml of a saturated solution of hydrogen chloride in dichloromethane are added. The mixture is stirred at RT for 30 min, during which the target product precipitates. The solvent is evaporated off and the remaining residue is stirred with 70 ml of diethyl ether. It is filtered off, and the residue on the filter is washed with diethyl ether and then dried under high vacuum. 893 mg (86% of theory) of the title compound result as colorless crystals.

HPLC (Method 7): $R_t$=5.1 min;

LC-MS (Method 12): $R_t$=1.47 min; MS (ESIpos): m/z=747 (M+H)$^+$;

$^1$H-NMR (400 MHz, DMSO-$d_6$): δ=0.94 and 0.95 (2d, 6H), 1.4 (m, 2H), 1.55 (m, 2H), 1.75 (m, 2H), 2.14 (m, 1H), 2.7-2.8 (m, 2H), 3.95 (m, 1H), 4.3-4.5 (m, 2H), 4.65 (s, 2H), 7.12 (d, 2H), 7.51 (d, 2H), 7.58 (d, 2H), 7.95 (d, 2H), 7.97 (s, 1H), 8.0 (m, 2H), 8.3 (m, 2H), 8.8 (d, 1H).

Example 2

2-{4-[2-Amino-6-({[2-(4-chlorophenyl)-1,3-thiazol-4-yl]methyl}thio)-3,5-dicyanopyridin-4-yl]-phenoxy}ethyl β-alanyl-L-valinate hydrochloride

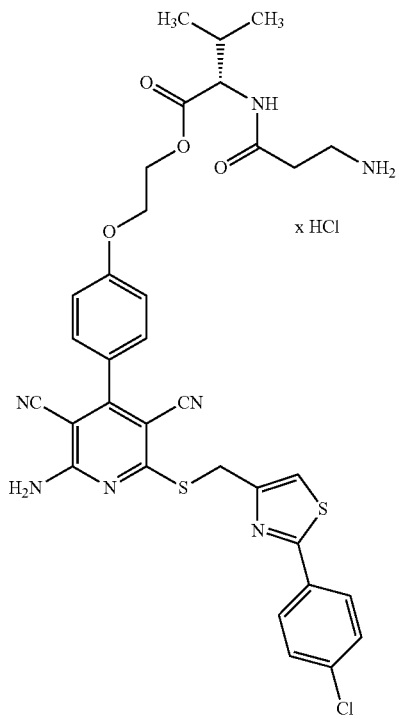 [SMILES: CC(C)[C@H](NC(=O)CCN)C(=O)OCCOc1ccc(-c2c(C#N)c(N)nc(SCc3csc(-c4ccc(Cl)cc4)n3)c2C#N)cc1]

0.1 g (0.12 mmol) of the compound from example 1A, 0.051 g (0.18 mmol) of 2,5-dioxopyrrolidin-1-yl N-(tert-butoxycarbonyl)-β-alaninate and 82 µl of N,N-diisopropylethylamine are mixed in 6 ml of DMF and stirred at room temperature overnight. The solvent is then removed in vacuo, and the residue is purified by flash chromatography on silica gel with dichloromethane/ethyl acetate as eluent (gradient 4:1→3:1→2:1). The appropriate fractions are combined, and the solvent is removed in vacuo. After the residue has been dried under high vacuum, 0.052 g (56% of theory) of the protected intermediate remains.

HPLC (Method 7): $R_t$=6.3 min.

0.05 g (0.063 mmol) of the resulting intermediate are taken up in 1 ml of dichloromethane and, while stirring, 15 ml of a saturated solution of hydrogen chloride in dichloromethane are added. The mixture is stirred at RT for 3 h, during which the target compound precipitates. The solvent is evaporated off and the remaining residue is stirred with 10 ml of diethyl ether. It is filtered off, and the residue on the filter is washed with diethyl ether and then dried under high vacuum. 41 mg (85% of theory) of the title compound result as colorless crystals.

HPLC (Method 7): $R_t$=5.2 min;

LC-MS (Method 12): $R_t$=2.1 min; MS (ESIpos): m/z=690 (M+H)$^+$;

$^1$H-NMR (400 MHz, DMSO-$d_6$): δ=0.89 and 0.9 (2d, 6H), 2.04 (m, 2H), 2.5 (m, 2H), 2.9-3.0 (m, 2H), 4.2 (m, 1H), 4.25 (m, 2H), 4.35-4.5 (m, 2H), 4.67 (s, 2H), 7.12 (d, 2H), 7.5 (d, 2H), 7.57 (d, 2H), 7.8 (m, 2H), 7.94 (s, 1H), 7.95 (d, 2H), 8.5 (d, 1H).

Example 3

2-{4-[2-Amino-6-({[2-(4-chlorophenyl)-1,3-thiazol-4-yl]methyl}thio)-3,5-dicyanopyridin-4-yl]-phenoxy}ethyl L-arginyl-L-valinate dihydrochloride

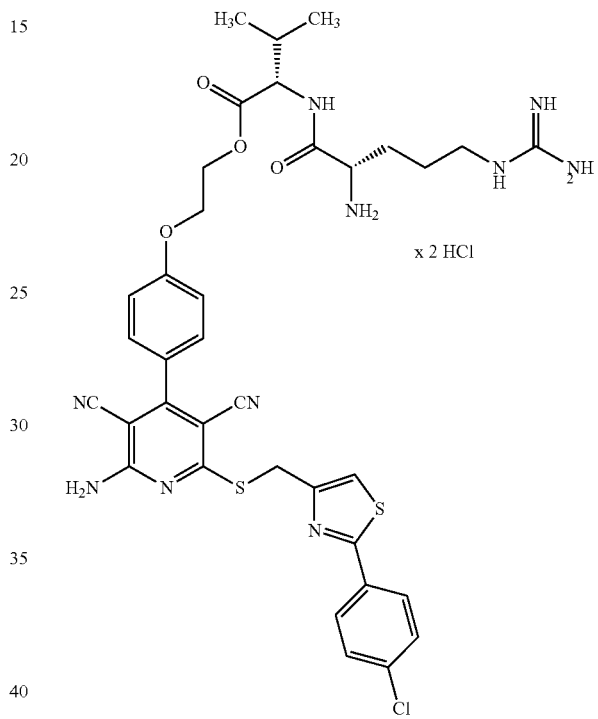

2.24 g (4.72 mmol) of N$^2$,N$^5$-bis(tert-butoxycarbonyl)-N$^5$-{[(tert-butoxycarbonyl)amino](imino)-methyl}-L-ornithine, 0.96 g (7.08 mmol) of 1-hydroxy-1H-benzotriazol hydrate and 1.09 g (5.66 mmol) of N-(3-dimethylaminopropyl)-N'-ethylcarbodiimide hydrochloride are mixed in 200 ml of DMF. After stirring for 30 min, 2 g (2.36 mmol) of the compound from example 1A and 1.65 ml of N,N-diisopropylethylamine are added, and the mixture is stirred at room temperature overnight. It is then concentrated and the remaining residue is stirred with water. It is filtered off with suction, and the residue is purified by flash chromatography on silica gel with dichloromethane/ethyl acetate as eluent (gradient 4:1→3:1). The appropriate fractions are combined and the solvent is removed in vacuo. After the residue has been dried under high vacuum, 1.12 g (44% of theory) of the protected intermediate remain.

HPLC (Method 7): $R_t$=6.1 min.

1.12 g (1.04 mmol) of the intermediate are taken up in 10 ml of dichloromethane, mixed with 10 ml of anhydrous trifluoroacetic acid and stirred at RT overnight. The mixture is then concentrated and the residue is stripped off twice with THF. It is filtered off, and the residue on the filter is taken up in a mixture of 25 ml of THF and 5 ml of methanol. While stirring, 20 ml of a 2 M solution of hydrogen chloride in diethyl ether are added. After brief further stirring, the precipitate which has separated out is filtered off with suction, and the residue on the filter is washed with diethyl ether. After drying under high vacuum, 920 mg (99% of theory) of the title compound remain as colorless crystals.

HPLC (Method 7): $R_t$=5.1 min;
LC-MS (Method 10): $R_t$=1.7 min; MS (ESIpos): m/z=775 (M+H)$^+$;
$^1$H-NMR (400 MHz, DMSO-d$_6$): δ=0.95 and 0.97 (2d, 6H), 1.6 (m, 2H), 1.75 (m, 2H), 2.14 (m, 1H), 3.25 (m, 2H), 4.05 (m, 1H), 4.25 (t, 1H), 4.3 (m, 2H), 4.4-4.5 (2 m, 2H), 4.65 (s, 2H), 7.12 (d, 2H), 7.48 (d, 2H), 7.58 (d, 2H), 7.95 (m, 3H), 8.4 (m, 2H), 8.9 (d, 1H).

Example 4

2-{4-[2-Amino-6-({[2-(4-chlorophenyl)-1,3-thiazol-4-yl]methyl}thio)-3,5-dicyanopyridin-4-yl]-phenoxy}ethyl L-lysyl-L-alaninate dihydrochloride

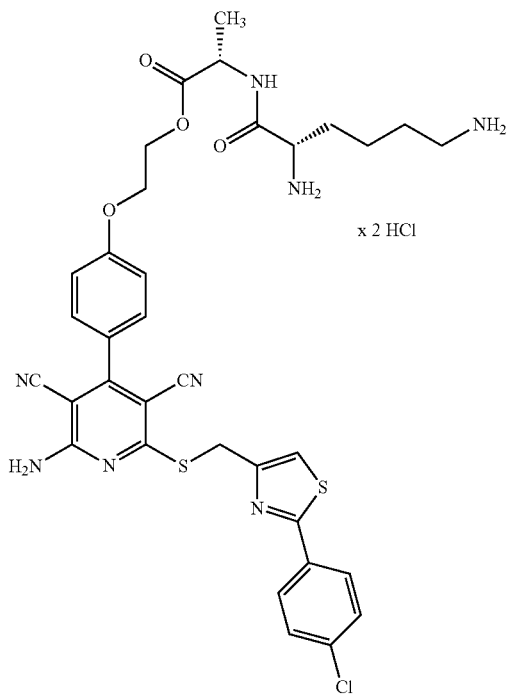 [SMILES: C[C@H](NC(=O)[C@@H](N)CCCCN)C(=O)OCCOc1ccc(-c2c(C#N)c(N)nc(SCc3csc(-c4ccc(Cl)cc4)n3)c2C#N)cc1]

1.2 g (1.7 mmol) of the compound from example 2A, 1.13 g (2.55 mmol) of 2,5-dioxopyrrolidin-1-yl-N$^2$,N$^6$-bis(tert-butoxycarbonyl)-L-lysinate and 1.5 ml of N,N-diisopropylethylamine are mixed in 40 ml of DMF and stirred at room temperature overnight. The mixture is then concentrated and the residue is partitioned between ethyl acetate and water. The organic phase is separated off and successively extracted twice with 5% strength citric acid and twice with 5% strength sodium bicarbonate solution. The organic phase is then concentrated and the residue is purified by flash chromatography on silica gel with dichloromethane/ethyl acetate as eluent (gradient 3:1→2:1).

The appropriate fractions are combined and the solvent is removed in vacuo. The residue is stirred with 50 ml of diethyl ether and 50 ml of pentane and filtered off with suction. After the residue has been dried under high vacuum, 1.14 g (73% of theory) of the protected intermediate remain.

HPLC (Method 7): $R_t$=6.4 min;
LC-MS (Method 11): $R_t$=2.64 min; MS (ESIpos): m/z=919 (M+H)$^+$.

1.14 g (1.24 mmol) of the intermediate are taken up in 10 ml of dichloromethane and, while stirring, 60 ml of a saturated solution of hydrogen chloride in dichloromethane are added. The mixture is stirred at RT overnight, during which the target compound precipitates. The solvent is concentrated to about one third of the volume, and the resulting suspension is mixed with 200 ml of diethyl ether. The solid is filtered off, and the residue on the filter is washed with diethyl ether and then dried under high vacuum. 1.0 g (quant.) of the title compound results as colorless crystals.

HPLC (Method 7): $R_t$=5.0 min;
LC-MS (Method 10): $R_t$=1.67 min; MS (ESIpos): m/z=719 (M+H)$^+$;
$^1$H-NMR (400 MHz, DMSO-d$_6$): δ=1.35 (d, 3H), 1.4 (m, 2H), 1.6 (m, 2H), 1.75 (m, 2H), 2.75 (m, 2H), 3.8 (m, 1H), 4.25 (m, 2H), 4.3-4.5 (m, 3H), 4.63 (s, 2H), 7.12 (d, 2H), 7.48 (d, 2H), 7.58 (d, 2H), 7.9-8.0 (m, 5H), 8.3 (m, 2H), 9.05 (d, 1H).

Example 5

2-{4-[2-Amino-6-({[2-(4-chlorophenyl)-1,3-thiazol-4-yl]methyl}thio)-3,5-dicyanopyridin-4-yl]-phenoxy}ethyl L-lysyl-L-serinate dihydrochloride

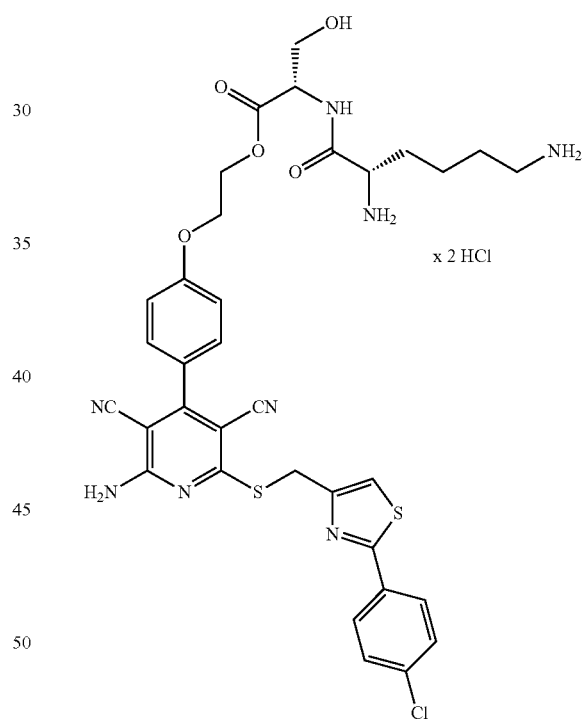

0.58 g (1.675 mmol) of N$^2$,N$^6$-bis(tert-butoxycarbonyl)-L-lysine, 0.28 g (1.83 mmol) of 1-hydroxy-1H-benzotriazole hydrate and 0.35 g (1.83 mmol) of N-(3-dimethylaminopropyl)-N'-ethylcarbodiimide hydrochloride are mixed in 40 ml of DMF and then 1.01 g (1.52 mmol) of the compound from example 3A are added. The mixture is stirred at room temperature overnight and then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is purified by flash chromatography on silica gel initially with dichloromethane/ethyl acetate as eluent (gradient 3:1→2:1); subsequent elution is with dichloromethane/ethyl acetate/methanol (150:50:5). The appropriate fractions are combined and concentrated. After the residue has been dried under high vacuum, 1.23 g (81% of theory) of the protected intermediate remain.

HPLC (Method 7): $R_t$=6.5 min;

LC-MS (Method 12): $R_t$=2.99 min; MS (ESIpos): m/z=991 (M+H)$^+$.

1.216 g (1.48 mmol) of the intermediate are taken up in 6 ml of dichloromethane, mixed with 6 ml of anhydrous trifluoroacetic acid and stirred at RT overnight. The mixture is then concentrated, and the residue is stripped off again with dichloromethane. It is filtered off, and the residue on the filter is taken up in a mixture of 25 ml of dichloromethane and 25 ml of ethyl acetate. While stirring, 20 ml of a 2 M solution of hydrogen chloride in diethyl ether are added. After brief further stirring, the precipitate which separates out is filtered off with suction, washed with diethyl ether and dried under high vacuum. The residue is then recrystallized from 20 ml of methanol and 20 ml of ethyl acetate. The precipitate is again filtered off with suction, washed with ethyl acetate and dried under high vacuum. 845 mg (70% of theory) of the title compound are obtained as colorless crystals.

HPLC (Method 7): $R_t$=4.9 min;

LC-MS (Method 10): $R_t$=1.62 min; MS (ESIpos): m/z=735 (M+H)$^+$.

Example 6

2-{4-[2-Amino-6-({[2-(4-chlorophenyl)-1,3-thiazol-4-yl]methyl}thio)-3,5-dicyanopyridin-4-yl]-phenoxy}ethyl N-(2-aminoethyl)-L-α-glutaminate dihydrochloride

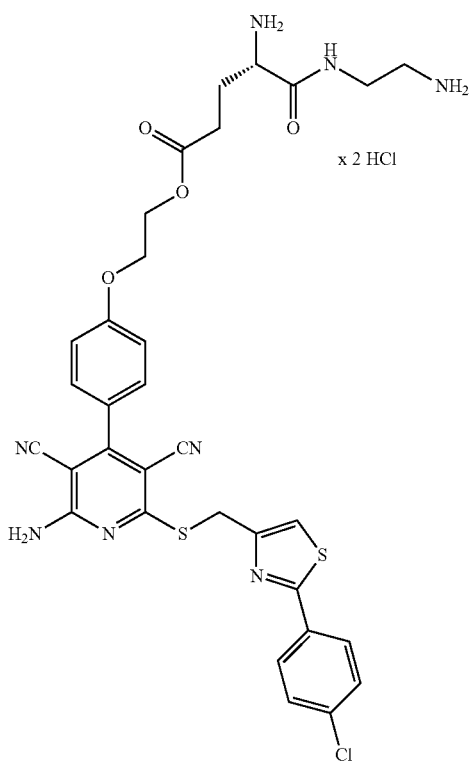 [SMILES: N#Cc1c(N)nc(SCc2csc(-c3ccc(Cl)cc3)n2)c(C#N)c1-c1ccc(OCCOC(=O)CC[C@H](N)C(=O)NCCN)cc1]

1 g (1.92 mmol) of 2-amino-6-({[2-(4-chlorophenyl)-1,3-thiazol-4-yl]methyl}thio)-4-[4-(2-hydroxy-ethoxy)phenyl]pyridine-3,5-dicarbonitrile, 0.824 g (2.11 mmol) of the compound from example 4A, 0.442 g (2.31 mmol) of 1-(3-dimethylaminopropyl)-3-ethylcarbodiimide hydrochloride and 0.024 g (0.19 mmol) of 4-dimethylaminopyridine are mixed in 40 ml of dichloromethane and 10 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is purified by flash chromatography on silica gel initially with dichloromethane/ethyl acetate (3:1) as eluent; subsequent elution is with dichloromethane/ethyl acetate/methanol (gradient 300:100:5→300:100:10). The appropriate fractions are combined and the solvent is removed in vacuo. After the residue has been dried under high vacuum, 1.52 g (89% of theory) of the protected intermediate remain.

HPLC (Method 7): $R_t$=6.0 min;

LC-MS (Method 11): $R_t$=2.54 min; MS (ESIpos): m/z=891 (M+H)$^+$.

1.518 g (1.7 mmol) of the intermediate are taken up in 5 ml of dichloromethane, mixed with 5 ml of anhydrous trifluoroacetic acid, and stirred at RT for 1 h. The mixture is then concentrated, and the residue is again stripped off with dichloromethane. The residue is then dissolved in 20 ml of ethyl acetate. While stirring, 20 ml of a 2 M solution of hydrogen chloride in diethyl ether are added. Brief subsequent stirring is followed by filtration with suction, and the residue on the filter is washed with diethyl ether and dried. 1300 mg (99% of theory) of the title compound are obtained. It is then recrystallized from 25 ml of methanol and 25 ml of ethyl acetate. The precipitate is again filtered off with suction, washed with ethyl acetate and then dried under high vacuum. 1080 mg (83% of theory) of the title compound remain.

HPLC (Method 7): $R_t$=4.9 min;

LC-MS (Method 10): $R_t$=1.59 min; MS (ESIpos): m/z=691 (M+H)$^+$;

$^1$H-NMR (400 MHz, DMSO-$d_6$): δ=2.05 (m, 2H), 2.45 (m, 2H), 2.85 and 2.95 (2 m, 2H), 3.25 and 3.5 (2 m, 2H), 3.7 (m, 1H), 4.3 (m, 2H), 4.4 (m, 2H), 4.65 (s, 2H), 7.12 (d, 2H), 7.48 (d, 2H), 7.58 (d, 2H), 7.93 (s, 1H), 7.94 (d, 2H), 8.1 (m, 3H), 8.45 (m, 3H), 8.95 (t, 1H).

Example 7

2-{4-[2-Amino-6-({[2-(4-chlorophenyl)-1,3-thiazol-4-yl]methyl}thio)-3,5-dicyanopyridin-4-yl]-phenoxy}ethyl N-(2-aminoethyl)-L-glutaminate dihydrochloride

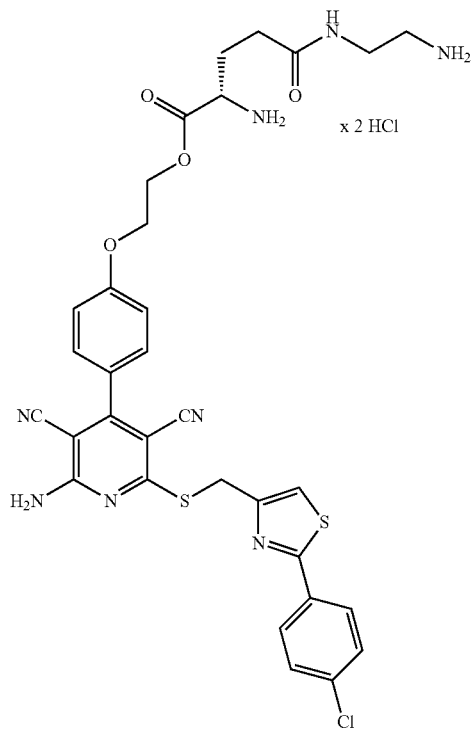 [SMILES: N#Cc1c(N)nc(SCc2csc(-c3ccc(Cl)cc3)n2)c(C#N)c1-c1ccc(OCCOC(=O)[C@@H](N)CCC(=O)NCCN)cc1]

1 g (1.92 mmol) of 2-amino-6-({[2-(4-chlorophenyl)-1,3-thiazol-4-yl]methyl}thio)-4-[4-(2-hydroxy-ethoxy)phenyl]pyridine-3,5-dicarbonitrile, 0.824 g (2.11 mmol) of the compound from example 5A, 0.442 g (2.31 mmol) of 1-(3-dimethylaminopropyl)-3-ethylcarbodiimide hydrochloride and 0.024 g (0.192 mmol) of 4-dimethylaminopyridine are mixed in 40 ml of dichloromethane and 10 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is precipitated from dichloromethane with diethyl ether. The precipitate is filtered off, washed with diethyl ether and dried under high vacuum. 1.5 g (87% of theory) of the protected intermediate remain.

HPLC (Method 7): $R_t$=6.0 min;
LC-MS (Method 10): $R_t$=3.12 min; MS (ESIpos): m/z=891 (M+H)$^+$.

1.5 g (1.7 mmol) of the intermediate are taken up in 20 ml of dichloromethane, mixed with 5 ml of anhydrous trifluoroacetic acid, and stirred at RT for 1 h. The mixture is then concentrated, and the residue is stripped off with toluene several times. The residue is then taken up in 15 ml of dichloromethane, 5 ml of ethyl acetate and 1 ml of methanol. While stirring, 20 ml of a 2 M solution of hydrogen chloride in diethyl ether are added. Brief subsequent stirring is followed by filtration with suction, and the residue on the filter is washed twice with diethyl ether and dried. The residue is then dissolved in 50 ml of dilute hydrochloric acid (pH 3) and lyophilized. 1265 mg (98% of theory) of the title compound remain.

HPLC (Method 7): $R_t$=4.9 min;
LC-MS (Method 11): $R_t$=1.19 min; MS (ESIpos): m/z=691 (M+H)$^+$.

Example 8

2-{4-[2-Amino-6-({[2-(4-chlorophenyl)-1,3-thiazol-4-yl]methyl}thio)-3,5-dicyanopyridin-4-yl]-phenoxy}ethyl N-(2-aminoethyl)-L-asparaginate dihydrochloride

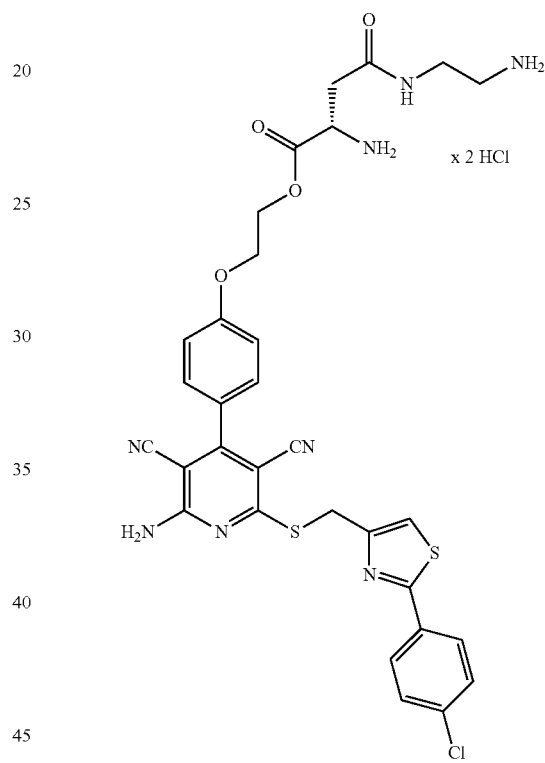

1 g (1.92 mmol) of 2-amino-6-({[2-(4-chlorophenyl)-1,3-thiazol-4-yl]methyl}thio)-4-[4-(2-hydroxy-ethoxy)phenyl]pyridine-3,5-dicarbonitrile, 0.794 g (2.12 mmol) of the compound from example 6A, 0.442 g (2.31 mmol) of 1-(3-dimethylaminopropyl)-3-ethylcarbodiimide hydrochloride and 0.024 g (0.192 mmol) of 4-dimethylaminopyridine are mixed in 40 ml of dichloromethane and 10 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is precipitated from dichloromethane with diethyl ether. The precipitate is filtered off, washed with diethyl ether and dried under high vacuum. 1.28 g (74% of theory) of the protected intermediate remain.

HPLC (Method 7): $R_t$=6.0 min;
LC-MS (Method 10): $R_t$=3.13 min; MS (ESIpos): m/z=877 (M+H)$^+$.

1.28 g (1.46 mmol) of the intermediate are taken up in 20 ml of dichloromethane, mixed with 5 ml of anhydrous trifluoroacetic acid, and stirred at RT for 1 h. The mixture is then concentrated, and the residue is stripped off several times with toluene. The residue is then taken up in 15 ml of dichloromethane, 5 ml of ethyl acetate and 1 ml of methanol. While stirring, 5 ml of a 2 M solution of hydrogen chloride in diethyl ether are added. Brief subsequent stirring is followed by filtration with suction, and the residue on the filter is washed twice with diethyl ether and dried. 1096 mg (quant.) of the title compound remain.

HPLC (Method 7): $R_t$=4.9 min;
LC-MS (Method 10): $R_t$=1.58 min; MS (ESIpos): m/z=677 (M+H)$^+$.

Example 9

(2S)-5-(2-{4-[2-Amino-6-({[2-(4-chlorophenyl)-1,3-thiazol-4-yl]methyl}thio)-3,5-dicyanopyridin-4-yl]phenoxy}ethoxy)-2-[(3-carboxypropanoyl)amino]-5-oxopentanoic acid

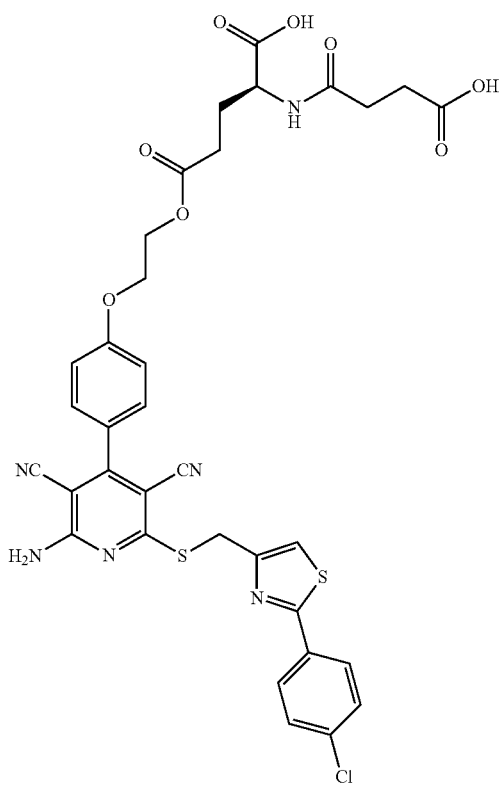 [SMILES: N#Cc1c(N)nc(SCc2csc(-c3ccc(Cl)cc3)n2)c(C#N)c1-c1ccc(OCCOC(=O)CC[C@H](NC(=O)CCC(=O)O)C(=O)O)cc1]

0.432 g (2.48 mmol) of 4-tert-butoxy-4-oxobutyric acid, 0.475 g (2.48 mmol) of 1-(3-dimethyl-aminopropyl)-3-ethylcarbodiimide hydrochloride, 0.380 g (2.48 mmol) of 1-hydroxy-1H-benzotriazole hydrate and 1.59 g (2.254 mmol) of the compound from example 7A are mixed in 70 ml of DMF and stirred at room temperature overnight. The mixture is then poured into a mixture of half-saturated ammonium chloride solution and ethyl acetate. The organic phase is separated off, washed successively with water, saturated sodium bicarbonate solution and saturated sodium chloride solution, dried over magnesium sulfate, filtered and concentrated. The residue is purified by flash chromatography on silica gel with dichloromethane/ethyl acetate as eluent (gradient 10:1→5: 1→3:1). The appropriate fractions are combined, and the solvent is removed in vacuo. The residue is then purified again in portions by preparative HPLC (method 6b). The appropriate fractions are combined, and the solvent is removed in vacuo. After the residue has been dried under high vacuum, 1.63 g (84% of theory) of the protected intermediate remain.

HPLC (Method 7): $R_t$=6.3 min;
LC-MS (Method 11): $R_t$=2.71 min; MS (ESIpos): m/z=861 (M+H)$^+$.

1.285 g (1.49 mmol) of the intermediate are taken up in 10 ml of dichloromethane, mixed with 10 ml of anhydrous trifluoroacetic acid, and stirred at RT for 1 h. The mixture is then concentrated, and the residue is stripped off several times with toluene. The remaining residue is then stirred with diethyl ether, and the precipitated solid is filtered off with suction and washed with diethyl ether. After drying under high vacuum, 1.06 g (95% of theory) of the title compound remain.

HPLC (Method 7): $R_t$=5.4 min;
LC-MS (Method 10): $R_t$=2.23 min; MS (ESIpos): m/z=749 (M+H)$^+$.

Example 10

(2S)-5-(2-{4-[2-Amino-6-({[2-(4-chlorophenyl)-1,3-thiazol-4-yl]methyl}thio)-3,5-dicyanopyridin-4-yl]phenoxy}ethoxy)-2-[(3-carboxypropanoyl)amino]-5-oxopentanoic acid disodium salt

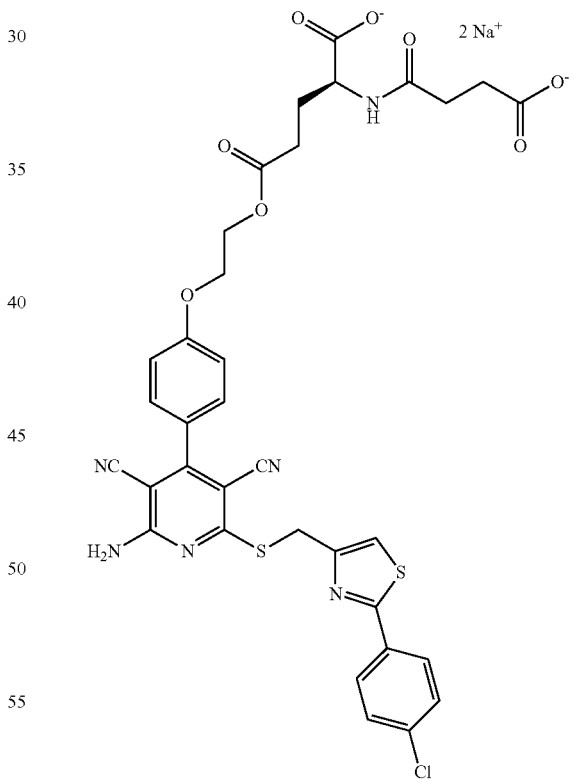

0.5 g (0.667 mmol) of the compound from example 9 is dissolved in 12.5 ml of acetonitrile and 62.5 ml of water, and 13 ml of 0.1 N sodium hydroxide solution are added. After brief stirring, the mixture is lyophilized. After drying under high vacuum, 0.53 g (quant.) of the title compound remain.

HPLC (Method 7): $R_t$=5.4 min;
LC-MS (Method 11): $R_t$=2.06 min; MS (ESIpos): m/z=749 (M+H)$^+$.

Example 11

2-{4-[2-Amino-6-({[2-(4-chlorophenyl)-1,3-thiazol-4-yl]methyl}sulfanyl)-3,5-dicyanopyridin-4-yl]-phenoxy}ethyl L-lysyl-L-leucinate dihydrochloride

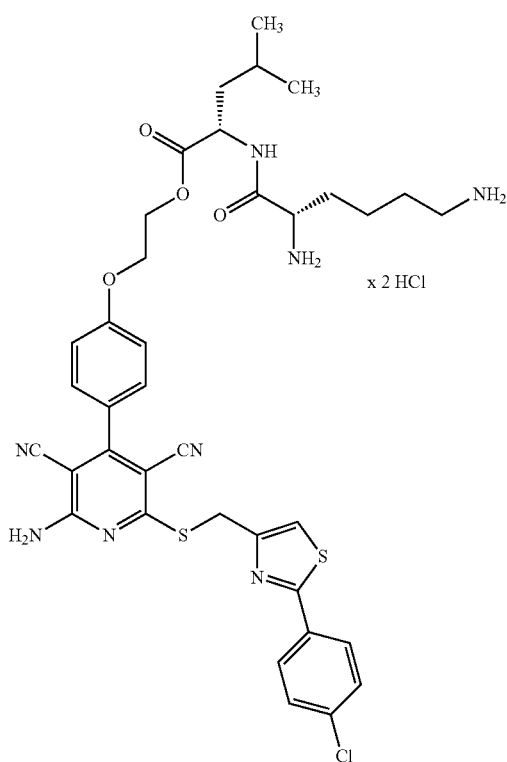 [SMILES: CC(C)C[C@H](NC(=O)[C@@H](N)CCCCN)C(=O)OCCOc1ccc(-c2c(C#N)c(N)nc(SCc3csc(-c4ccc(Cl)cc4)n3)c2C#N)cc1]

0.928 g (2.68 mmol) of $N^2,N^6$-bis(tert-butoxycarbonyl)-L-lysine, 0.362 g (2.68 mmol) of 1-hydroxy-1H-benzotriazole hydrate and 0.411 g (2.144 mmol) of N-(3-dimethylaminopropyl)-N'-ethylcarbodiimide hydrochloride are mixed in 200 ml of DMF. Then 1.335 g (1.787 mmol) of the compound from example 8A and 935 µl of N,N-diisopropylethylamine are added, and the mixture is stirred at room temperature overnight. It is subsequently concentrated in vacuo, and the residue is taken up in ethyl acetate and extracted successively with water, with 5% strength citric acid and twice with 5% strength sodium bicarbonate solution. The organic phase is concentrated and the residue is purified by flash chromatography on silica gel with dichloromethane/ethyl acetate as eluent (gradient 3:1→2:1). The appropriate fractions are combined, and the solvent is removed in vacuo. After the residue has been dried under high vacuum, 1.39 g (81% of theory) of the protected intermediate remain.

HPLC (Method 7): $R_t$=6.8 min.

1.385 g (1.44 mmol) of the resulting intermediate are taken up in 20 ml of dichloromethane and, while stirring, 50 ml of a saturated solution of hydrogen chloride in dichloromethane are added. The mixture is stirred at RT for 1 h, during which the target product precipitates. The solvent is evaporated off and the remaining residue is mixed with 70 ml of pentane, briefly stirred and then filtered off with suction. Drying under high vacuum results in 1.17 g (97% of theory) of the title compound.

HPLC (Method 7): $R_t$=5.17 min;
LC-MS (Method 10): $R_t$=1.76 min; MS (ESIpos): m/z=761 (M+H)$^+$.

Example 12

2-{4-[2-Amino-6-({[2-(4-chlorophenyl)-1,3-thiazol-4-yl]methyl}sulfanyl)-3,5-dicyanopyridin-4-yl]-phenoxy}ethyl L-lysyl-D-alaninate dihydrochloride

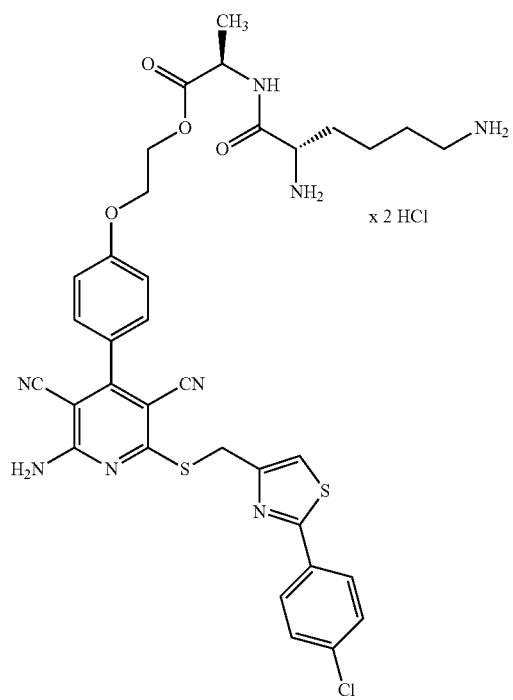 [SMILES: C[C@@H](NC(=O)[C@@H](N)CCCCN)C(=O)OCCOc1ccc(-c2c(C#N)c(N)nc(SCc3csc(-c4ccc(Cl)cc4)n3)c2C#N)cc1]

0.59 g (1.702 mmol) of $N^2,N^6$-bis(tert-butoxycarbonyl)-L-lysine, 0.345 g (2.553 mmol) of 1-hydroxy-1H-benzotriazole hydrate and 0.391 g (2.042 mmol) of N-(3-dimethylaminopropyl)-N'-ethylcarbodiimide hydrochloride are mixed in 24 ml of DMF. After stirring at RT for 5 min, 1.2 g (1.702 mmol) of the compound from example 9A and 1.5 ml of N,N-diisopropylethylamine are added, and the mixture is stirred at room temperature overnight. It is then concentrated, and the residue is partitioned between 500 ml of ethyl acetate and 500 ml of water. The organic phase is separated off and extracted successively three times with 5% strength citric acid and three times with 10% strength sodium bicarbonate solution. The organic phase is then concentrated and the residue is purified by flash chromatography on silica gel with dichloromethane/ethyl acetate as eluent (gradient 2:1→1:1). The appropriate fractions are combined and the solvent is removed in vacuo. The residue is stirred with 30 ml of ethyl acetate and then mixed with 100 ml of diethyl ether. The product is filtered off with suction, and the remaining residue is washed with diethyl ether. After drying under high vacuum, 0.773 g (49% of theory) of the protected intermediate remain.

HPLC (Method 7): $R_t$=6.1 min.

0.74 g (0.805 mmol) of the resulting intermediate are taken up in 200 ml of dichloromethane. Hydrogen chloride gas is passed into this solution while stirring. The deprotected title compound precipitates during this. Stirring is continued at RT, and the reaction is complete after 1 h. The mixture is concentrated to half the volume in vacuo, and the precipitate is filtered off. The residue on the filter is washed with diethyl ether and then dried under high vacuum at 100° C. 539 mg (85% of theory) of the title compound are obtained in this way as colorless crystals.

HPLC (Method 7): $R_t$=5.0 min;

LC-MS (Method 13): $R_t$=1.04 min; MS (ESIpos): m/z=719 (M+H)$^+$;

$^1$H-NMR (400 MHz, DMSO-d$_6$): δ=1.3 (d, 3H), 1.35 (m, 2H), 1.52 (m, 2H), 1.75 (m, 2H), 2.75 (m, 2H), 3.8 (m, 1H), 4.3 (m, 2H), 4.3-4.5 (m, 3H), 4.63 (s, 2H), 7.12 (d, 2H), 7.48 (d, 2H), 7.58 (d, 2H), 7.8-8.0 (m, 5H), 8.25 (m, 2H), 9.0 (d, 1H).

Example 13

2-{4-[2-Amino-6-({[2-(4-chlorophenyl)-1,3-thiazol-4-yl]methyl}sulfanyl)-3,5-dicyanopyridin-4-yl]-phenoxy}ethyl N-(2-aminoethyl)-D-α-glutaminate dihydrochloride

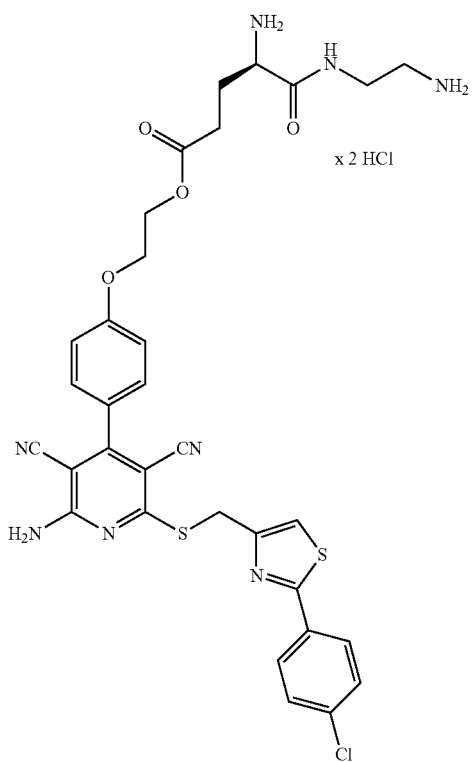 [SMILES: N#Cc1c(N)nc(SCc2csc(-c3ccc(Cl)cc3)n2)c(C#N)c1-c1ccc(OCCOC(=O)CC[C@@H](N)C(=O)NCCN)cc1]

0.522 g (1.0 mmol) of 2-amino-6-({[2-(4-chlorophenyl)-1,3-thiazol-4-yl]methyl}thio)-4-[4-(2-hydroxyethoxy)phenyl]pyridine-3,5-dicarbonitrile, 0.430 g (1.104 mmol) of the compound from example 10A, 0.231 g (1.204 mmol) of 1-(3-dimethylaminopropyl)-3-ethylcarbodiimide hydrochloride and 0.012 g (0.1 mmol) of 4-dimethylaminopyridine are mixed in 20 ml of dichloromethane and 5 ml of DMF and stirred at room temperature overnight. The mixture is then poured into a mixture of half-saturated ammonium chloride solution and dichloromethane. The organic phase is separated off, washed successively with water, saturated sodium bicarbonate solution and saturated sodium chloride solution, dried over magnesium sulfate, filtered and concentrated. The residue is purified by flash chromatography on silica gel firstly with dichloromethane/ethyl acetate (3:1) as eluent; subsequent elution is with dichloromethane/ethyl acetate/methanol (gradient 300:100:5→300:100:10). The appropriate fractions are combined and the solvent is removed in vacuo. After the residue has been dried under high vacuum, 0.711 g (79% of theory) of the protected intermediate remains.

HPLC (Method 7): $R_t$=6.0 min;

LC-MS (Method 13): $R_t$=1.54 min; MS (ESIpos): m/z=891 (M+H)$^+$.

0.711 g (0.798 mmol) of the resulting intermediate are taken up in 4 ml of dichloromethane, mixed with 4 ml of anhydrous trifluoroacetic acid, and stirred at RT for 1 h. The mixture is then concentrated, and the residue is again stripped off with dichloromethane. The residue is then dissolved in 50 ml of ethyl acetate. While stirring, 20 ml of a 2 M solution of hydrogen chloride in diethyl ether are added. Brief subsequent stirring is followed by filtration with suction, and the residue on the filter is washed with diethyl ether and dried. 590 mg (97% of theory) of the title compound are obtained.

HPLC (Method 7): $R_t$=4.9 min;

LC-MS (Method 11): $R_t$=1.22 min; MS (ESIpos): m/z=691 (M+H)$^+$;

$^1$H-NMR (400 MHz, DMSO-d$_6$): δ=2.05 (m, 2H), 2.45 (m, 2H), 2.85 and 2.95 (2 m, 2H), 3.25 and 3.5 (2 m, 2H), 3.7 (m, 1H), 4.3 (m, 2H), 4.4 (m, 2H), 4.65 (s, 2H), 7.12 (d, 2H), 7.48 (d, 2H), 7.58 (d, 2H), 7.93 (s, 1H), 7.94 (d, 2H), 8.1 (m, 3H), 8.45 (m, 3H), 8.93 (t, 1H).

Example 14

2-{4-[2-Amino-6-({[2-(4-chlorophenyl)-1,3-thiazol-4-yl]methyl}sulfanyl)-3,5-dicyanopyridin-4-yl]-phenoxy}ethyl L-arginyl-L-alaninate dihydrochloride

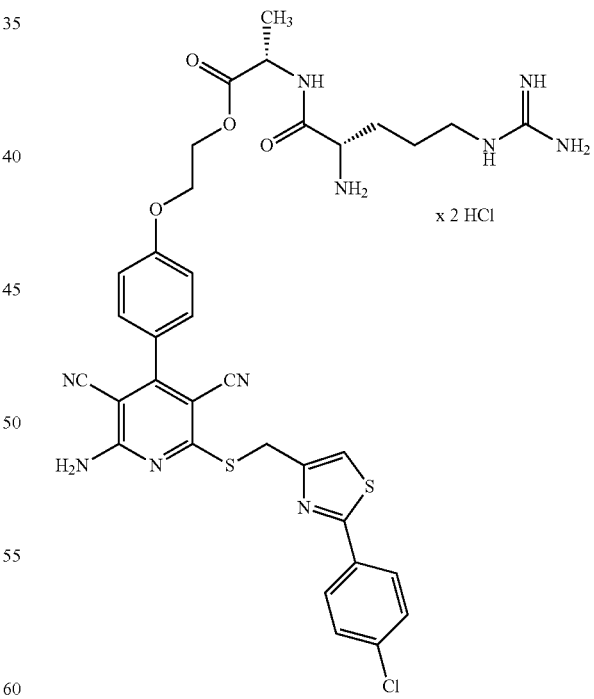

0.269 g (0.567 mmol) of N$^5$-[N,N'-bis(tert-butoxycarbonyl)carbamidoyl]-N$^2$-(tert-butoxycarbonyl)-L-ornithine, 0.115 g (0.851 mmol) of 1-hydroxy-1H-benzotriazole hydrate and 0.131 g (0.681 mmol) of N-(3-dimethylaminopropyl)-N'-ethylcarbodiimide hydrochloride are mixed in 20 ml of DMF. After stirring for 30 min, 0.2 g (0.284 mmol) of the compound from example 2A and 200 µl of N,N-diisopropylethylamine are added, and the mixture is stirred at room temperature overnight. It is then concentrated in vacuo, and the residue is taken up in dichloromethane and extracted successively with 5% strength citric acid, 5% strength sodium bicarbonate solution and water. The organic phase is concentrated and the residue is purified by flash chromatography on silica gel with dichloromethane/ethyl acetate (3:1) as eluent. The appropriate fractions are combined, and the solvent is removed in vacuo. After the residue has been dried under high vacuum, 0.179 g (60% of theory) of the protected intermediate remains.

HPLC (Method 7): $R_t$=5.8 min.

0.178 g (0.17 mmol) of the resulting intermediate are taken up in 30 ml of a saturated solution of hydrogen chloride in dichloromethane and stirred at RT overnight. The mixture is concentrated to half the volume in vacuo, and the resulting precipitate is filtered off. The residue on the filter is washed with diethyl ether and then dried under high vacuum. 119 mg (82% of theory) of the title compound are obtained as colorless crystals in this way.

HPLC (Method 7): $R_t$=4.9 min;
LC-MS (Method 10): $R_t$=1.58 min; MS (ESIpos): m/z=747 (M+H)$^+$;
$^1$H-NMR (400 MHz, DMSO-$d_6$): δ=1.35 (d, 3H), 1.55 (m, 2H), 1.75 (m, 2H), 3.25 (m, 2H), 3.85 (m, 1H), 4.25 (m, 2H), 4.3-4.5 (m, 3H), 4.65 (s, 2H), 7.12 (d, 2H), 7.48 (d, 2H), 7.58 (d, 2H), 7.75 (t, 1H), 7.93 (s, 1H), 7.94 (d, 2H), 8.3 (m, 3H), 9.1 (d, 1H).

Example 15

2-{4-[2-Amino-6-({[2-(4-chlorophenyl)-1,3-thiazol-4-yl]methyl}sulfanyl)-3,5-dicyanopyridin-4-yl]-phenoxy}ethyl L-histidyl-L-alaninate dihydrochloride

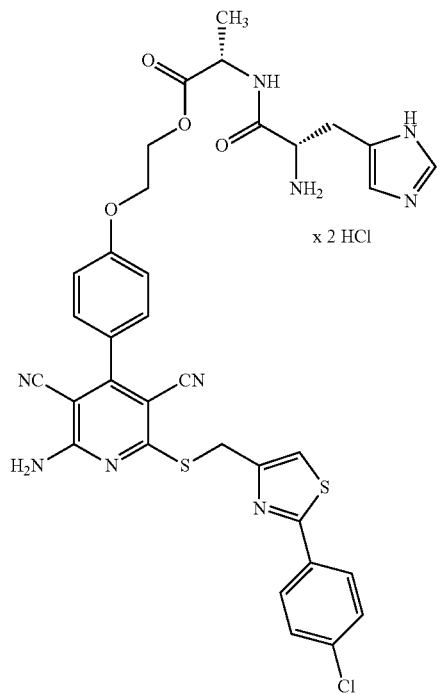 [SMILES: C[C@H](NC(=O)[C@@H](N)Cc1cnc[nH]1)C(=O)OCCOc1ccc(-c2c(C#N)c(N)nc(SCc3csc(-c4ccc(Cl)cc4)n3)c2C#N)cc1]

0.145 g (0.567 mmol) of N-(tert-butoxycarbonyl)-L-histidine, 0.115 g (0.851 mmol) of 1-hydroxy-1H-benzotriazol hydrate and 0.131 g (0.681 mmol) of N-(3-dimethylaminopropyl)-N'-ethylcarbodiimide hydrochloride are mixed in 20 ml of DMF. After stirring for 30 min, 0.2 g (0.284 mmol) of the compound from example 2A and 200 µl of N,N-diisopropylethylamine are added, and the mixture is stirred at room temperature overnight. It is then concentrated in vacuo, and the residue is taken up in dichloromethane and extracted successively with 5% strength citric acid, 5% strength sodium bicarbonate solution and water. The organic phase is concentrated, and the residue is purified by flash chromatography on silica gel with toluene/ethanol (3:1) as eluent. The appropriate fractions are combined, and the solvent is removed in vacuo. After the residue has been dried under high vacuum, 0.206 g (88% of theory) of the protected intermediate remains.

HPLC (Method 7): $R_t$=5.3 min.

0.206 g (0.249 mmol) of the resulting intermediate are taken up in 30 ml of a saturated solution of hydrogen chloride in dichloromethane and stirred at RT for 2 h. The mixture is concentrated to half the volume in vacuo, and the resulting precipitate is filtered off. The residue on the filter is washed with diethyl ether and then dried under high vacuum. 171 mg (90% of theory) of the title compound are obtained as colorless crystals in this way.

HPLC (Method 7): $R_t$=4.8 min;
LC-MS (Method 10): $R_t$=1.59 min; MS (ESIpos): m/z=728 (M+H)$^+$;
$^1$H-NMR (400 MHz, DMSO-$d_6$): δ=1.35 (d, 3H), 3.15 and 3.25 (2 dd, 2H), 4.25 (m, 3H), 4.3-4.5 (m, 3H), 4.65 (s, 2H), 7.12 (d, 2H), 7.4 (s, 1H), 7.48 (d, 2H), 7.58 (d, 2H), 7.93 (s, 1H), 7.94 (d, 2H), 8.5 (m, 3H), 9.05 (s, 1H), 9.2 (d, 1H).

Example 16

2-{4-[2-Amino-6-({[2-(4-chlorophenyl)-1,3-thiazol-4-yl]methyl}sulfanyl)-3,5-dicyanopyridin-4-yl]-phenoxy}ethyl N-[(2S)-2,4-diaminobutanoyl]-L-alaninate dihydrochloride

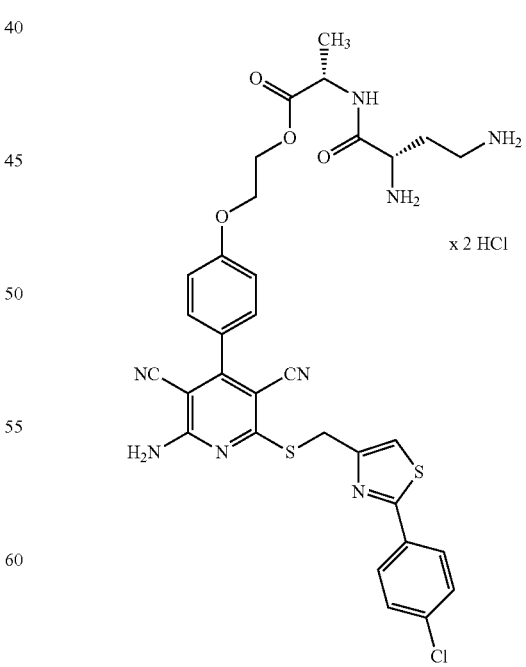

0.181 g (0.567 mmol) of (2S)-2,4-bis[(tert-butoxycarbonyl)amino]butyric acid, 0.115 g (0.851 mmol) of 1-hydroxy- 1H-benzotriazol hydrate and 0.131 g (0.681 mmol) of N-(3-dimethyl-aminopropyl)-N'-ethylcarbodiimide hydrochloride are mixed in 20 ml of DMF. After stirring at RT for 30 min, 0.2 g (0.284 mmol) of the compound from example 2A and 200 μl of N,N-diisopropylethylamine are added, and the mixture is stirred at room temperature overnight. It is then concentrated in vacuo, and the residue is taken up in dichloromethane and extracted successively with 5% strength citric acid, 5% strength sodium bicarbonate solution and water. The organic phase is concentrated and the residue is purified by flash chromatography on silica gel with toluene/ethanol (10:1) as eluent. The appropriate fractions are combined, and the solvent is removed in vacuo. After the residue has been dried under high vacuum, 0.217 g (86% of theory) of the protected intermediate remains.

HPLC (Method 7): $R_t$=6.3 min.

0.212 g (0.238 mmol) of the resulting intermediate is taken up in 25 ml of a saturated solution of hydrogen chloride in dichloromethane and stirred at RT for 1.5 h. The mixture is concentrated to half the volume in vacuo, and the resulting precipitate is filtered off. The residue on the filter is washed with diethyl ether and then dried under high vacuum. 171 mg (94% of theory) of the title compound are obtained as colorless crystals in this way.

HPLC (Method 7): $R_t$=4.8 min;

LC-MS (Method 10): $R_t$=1.56 min; MS (ESIpos): m/z=691 (M+H)$^+$.

Example 17

2-{4-[2-Amino-6-({[2-(4-chlorophenyl)-1,3-thiazol-4-yl]methyl}sulfanyl)-3,5-dicyanopyridin-4-yl]-phenoxy}ethyl L-lysylglycinate dihydrochloride

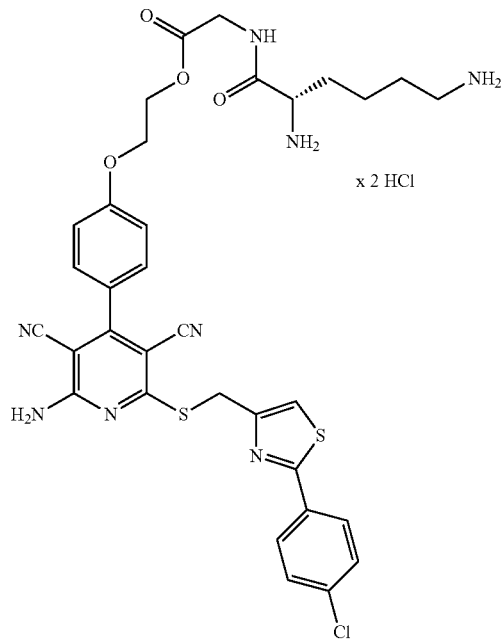 [SMILES: N#Cc1c(N)nc(SCc2csc(-c3ccc(Cl)cc3)n2)c(C#N)c1-c1ccc(OCCOC(=O)CNC(=O)[C@@H](N)CCCCN)cc1]

0.185 g (0.535 mmol) of $N^2$,$N^6$-bis(tert-butoxycarbonyl)-L-lysine, 0.108 g (0.803 mmol) of 1-hydroxy-1H-benzotriazole hydrate and 0.123 g (0.642 mmol) of N-(3-dimethylaminopropyl)-N'-ethylcarbodiimide hydrochloride are mixed in 15 ml of DMF and stirred at RT for 5 min. Then 0.37 g (0.535 mmol) of the compound from example 11A and 466 μl of N,N-diisopropylethylamine are added, and the mixture is stirred at room temperature overnight. It is then concentrated in vacuo, and the residue is partitioned between 500 ml of ethyl acetate and 200 ml of water. The organic phase is separated off, extracted successively three times with 5% strength citric acid and three times with 5% strength sodium bicarbonate solution and dried over magnesium sulfate. The organic phase is concentrated, and the residue is stirred with 50 ml of ethyl acetate for 10 min. Then 100 ml of diethyl ether are slowly added, and the precipitate is filtered off with suction. After drying under high vacuum, 0.303 g (63% of theory) of the protected intermediate remains.

HPLC (Method 7): $R_t$=6.1 min.

0.279 g (0.308 mmol) of the resulting intermediate is taken up in 120 ml of dichloromethane. Hydrogen chloride gas is passed into this solution while stirring, during which the deprotected title compound precipitates. The mixture is then stirred at RT for 1 h. It is then concentrated to half the volume in vacuo, and 30 ml of absolute THF are slowly added. After stirring for a further 15 min, the precipitate is filtered off. The residue on the filter is washed with diethyl ether and then dried under high vacuum. 212 mg (88% of theory) of the title compound are obtained in this way as colorless crystals.

HPLC (Method 7): $R_t$=4.8 min;

LC-MS (Method 10): $R_t$=1.52 min; MS (ESIpos): m/z=705 (M+H)$^+$.

Example 18

2-{4-[2-Amino-6-({[2-(4-chlorophenyl)-1,3-thiazol-4-yl]methyl}sulfanyl)-3,5-dicyanopyridin-4-yl]-phenoxy}ethyl L-lysyl-L-phenylalaninate dihydrochloride

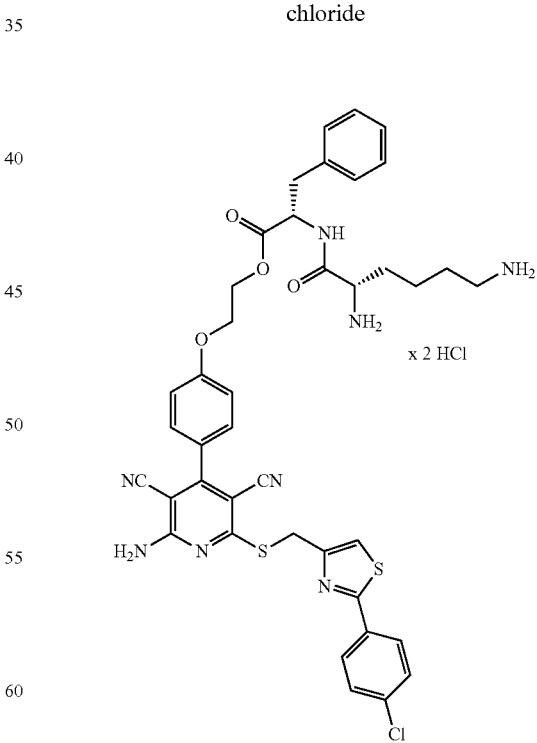

0.166 g (0.48 mmol) of $N^2$,$N^6$-bis(tert-butoxycarbonyl)-L-lysine, 0.097 g (0.72 mmol) of 1-hydroxy-1H-benzotriazole hydrate and 0.110 g (0.576 mmol) of N-(3-dimethylaminopropyl)-N'-ethylcarbodiimide hydrochloride are mixed in 7 ml of DMF and stirred at RT for 5 min. Then 0.375 g (0.48 mmol) of the compound from example 12A and 418 µl of N,N-diisopropylethylamine are added, and the mixture is stirred at room temperature overnight. It is then concentrated in vacuo, and the residue is taken up in 200 ml of ethyl acetate, extracted successively twice with 10% strength citric acid and twice with 10% strength sodium bicarbonate solution and dried over magnesium sulfate. The organic phase is concentrated, the residue is taken up in 10 ml of ethyl acetate, and the product is precipitated by adding diethyl ether. The precipitate is filtered off with suction and dried under high vacuum. 0.338 g (71% of theory) of the protected intermediate remains.

HPLC (Method 7): $R_t$=6.7 min.

0.32 g (0.321 mmol) of the resulting intermediate is taken up in 100 ml of dichloromethane. Hydrogen chloride gas is passed into this solution while stirring, during which the deprotected title compound precipitates. The mixture is stirred at RT for a further 1 h and then concentrated to half the volume in vacuo, and 10 ml absolute THF are slowly added. After stirring for a further 15 min, the precipitate is filtered off. The residue on the filter is washed with diethyl ether and then dried under high vacuum. 188 mg (67% of theory) of the title compound are obtained as colorless crystals in this way.

HPLC (Method 7): $R_t$=5.0 min;

LC-MS (Method 11): $R_t$=1.33 min; MS (ESIpos): m/z=795 $(M+H)^+$.

B. Determination of Solubility, Stability and Liberation Behavior a) Determination of the Solubility:

The test substance is suspended in 5% strength aqueous dextrose solution. This suspension is shaken at room temperature for 24 h. After ultracentrifugation at 224 000 g for 30 min, the supernatant is diluted with DMSO and analysed by HPLC. A two-point calibration plot of the test compound in DMSO is used for quantification.

HPLC Method for Acids:

Agilent 1100 with DAD (G1315A), quat. Pump (G1311A), autosampler CTC HTS PAL, degasser (G1322A) and column thermostat (G1316A); column: Phenomenex Gemini C18, 5 µm, 50 mm×2 mm; temperature: 40° C.; eluent A: water/phosphoric acid pH 2, eluent B: acetonitrile; flow rate: 0.7 ml/min; gradient: 0-0.5 min 85% A, 15% B; ramp 0.5-3 min 10% A, 90% B; 3-3.5 min 10% A, 90% B; ramp 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 3.5 µm, 60 mm×2.1 mm; temperature: 30° C.; eluent A: water+5 ml of perchloric acid/liter, eluent B: acetonitrile; flow rate: 0.75 ml/min; gradient: 0-0.5 min 98% A, 2% B; ramp 0.5-4.5 min 10% A, 90% B; 4.5-6 min 10% A, 90% B; ramp 6.5-6.7 min 98% A, 2% B; 6.7-7.5 min 98% A, 2% B.

The solubilities of representative exemplary embodiments in 5% strength aqueous dextrose solution are shown in Table 1:

TABLE 1

| Example No. | Solubility [mg/Liter] |
| --- | --- |
| 1 | >500 |
| 3 | 450 |
| 4 | >500 |

TABLE 1-continued

| Example No. | Solubility [mg/Liter] |
| --- | --- |
| 5 | >500 |
| 6 | >500 |
| 7 | 100 |
| 10 | 390 |
| 11 | >500 |
| 12 | >500 |
| 13 | >500 |
| 14 | >500 |
| 15 | 450 |
| 17 | >500 |
| 18 | 450 |

No decomposition of the exemplary compounds in these solutions is observed.

The solubility of the underlying active substance [compound (A)] in 5% strength aqueous dextrose solution is determined in this test to be <0.1 mg/liter.

b) Stability in Buffer at Various pH Values:

0.3 mg of the test substance is weighed into a 2 ml HPLC vial and 0.5 ml of acetonitrile or acetonitrile/DMSO (9:1) is added. The substance is dissolved by putting the sample vessel in an ultrasonic bath for about 10 seconds. Then 0.5 ml of the respective buffer solution is added, and the sample is again treated in the ultrasonic bath.

(Buffer) Solutions Employed:

pH 2: 0.03 mol of citric acid, 0.061 mol of sodium chloride and 0.0082 mol of hydrochoric acid ad 1 liter of water;

pH 4: 1 liter of Millipore water is adjusted to pH 4.0 with 1 N hydrochloric acid;

pH 5: 0.096 mol of citric acid and 0.2 mol of sodium hydroxide ad 1 liter of water;

pH 6: 0.06 mol of citric acid and 0.16 mol of sodium hydroxide ad 1 liter of water;

pH 7.4: 90.0 g of sodium chloride, 13.61 g of potassium dihydrogen phosphate and 83.35 g of 1 N sodium hydroxide solution are made up to 1 liter with water; this solution is then further diluted 1:10 with Millipore water.

pH 8: 0.013 mol of borax and 0.021 mol of hydrochloric acid ad 1 liter of water.

5 µl portions of the test solution are analyzed by HPLC for their content of unchanged test substance, and of parent substance (A) produced, every hour over a period of 24 hours at 37° C. The percentage areas of the appropriate peaks are used for quantification.

HPLC Method:

Agilent 1100 with DAD (G1314A), binary pump (G1312A), autosampler (G1329A), column oven (G1316A), thermostat (G1330A); column: Kromasil 100 C18, 125 mm×4.6 mm, 5 µm; column temperature: 30° C.; eluent A: water+5 ml of perchloric acid/liter, eluent B: acetonitrile; gradient: 0-2.0 min 90% A, 10% B; 2.0-18.0 min 64% A, 36% B; 18.0-20.0 min 64% A, 36% B; 20.0-21.0 min 10% A, 90% B; 21.0-23.0 min 90% A, 10% B; 23.0-26.0 min 90% A, 10% B; flow rate: 2.0 ml/min; UV detection: 294 nm.

The ratios of the peak areas (F) at the respective time points in relation to the peak areas at the starting time are shown in Table 2 for representative exemplary embodiments:

TABLE 2

| Example No. | pH | % test substance after 4 h [F(t = 4 h) × 100/ F(t = 0 h)] | % test substance after 24 h [F(t = 24 h) × 100/ F(t = 0 h)] |
| --- | --- | --- | --- |
| 1 | 4 | 100 | 100 |
| 1 | 6 | 100 | 100 |
| 1 | 7.4 | 99 | 96 |
| 1 | 8 | 99 | 90 |

TABLE 2-continued

| Example No. | pH | % test substance after 4 h [F(t = 4 h) × 100/ F(t = 0 h)] | % test substance after 24 h [F(t = 24 h) × 100/ F(t = 0 h)] |
|---|---|---|---|
| 2 | 4 | 100 | 100 |
| 2 | 7.4 | 100 | 100 |
| 3 | 4 | 100 | 100 |
| 3 | 7.4 | 99 | 55 |
| 4 | 4 | 100 | 100 |
| 4 | 5 | 100 | 98 |
| 4 | 6 | 97 | 84 |
| 4 | 7.4 | 48 | 2 |
| 5 | 4 | 100 | 100 |
| 5 | 5 | 100 | 98 |
| 5 | 6 | 95 | 70 |
| 6 | 2 | 100 | 100 |
| 6 | 4 | 100 | 100 |
| 6 | 5 | 96 | 80 |
| 6 | 6 | 78 | 25 |
| 6 | 7.4 | 8 | 0 |
| 7 | 4 | 100 | 98 |
| 7 | 7.4 | 51 | 2 |
| 9 | 4 | 100 | 100 |
| 9 | 7.4 | 100 | 100 |
| 10 | 4 | 100 | 99 |
| 10 | 7.4 | 100 | 99 |
| 11 | 4 | 100 | 100 |
| 11 | 7.4 | 90 | 55 |
| 12 | 4 | 99 | 98 |
| 12 | 7.4 | 49 | 2 |
| 13 | 4 | 100 | 99 |
| 13 | 7.4 | 24 | 0 |
| 14 | 4 | 100 | 100 |
| 14 | 7.4 | 68 | 8 |

In this test there is found to be a decrease in the content of test substance at the same time as an increase in the active ingredient compound (A).

c) In Vitro Stability in Rat and Human Plasma:

1 mg of the test substance is weighed into a 2 ml HPLC vial, and 1.5 ml of DMSO and 1 ml of water are added. The substance is dissolved by placing the sample vessel in an ultrasonic bath for about 10 seconds. 0.5 ml of rat or human plasma at 37° C. is added to 0.5 ml of this solution. The sample is shaken, and about 10 µl are removed for a first analysis (time point $t_0$). 4-6 further aliquots are removed for quantification in the period up to 2 hours after the start of incubation. The sample is kept at 37° C. during the time of the test. Characterization and quantification take place by HPLC.

HPLC Method:

Agilent 1100 with DAD (G1314A), binary pump (G1312A), autosampler (G1329A), column oven (G1316A), thermostat (G1330A); column: Kromasil 100 C18, 250 mm×4 mm, 5 µm; column temperature: 30° C.; eluent A: water+5 ml of perchloric acid/liter, eluent B: acetonitrile; gradient: 0-8.0 min 53% A, 47% B; 8.0-18.0 min 53% A, 47% B; 18.0-20.0 min 90% A, 10% B; 20.0-21.0 min 90% A, 10% B; 21.0-22.5 min 98% A, 2% B; 22.5-25.0 min 98% A, 2% B; flow rate: 2 ml/min; UV detection: 294 nm.

Table 3 indicates the respective times for representative exemplary embodiments at which 50% of the maximum possible amount of active ingredient compound (A) have been produced ($t_{50\%\ A}$) after incubation with rat plasma. For the evaluation, the ratio of the peak areas at the individual time points compared with the starting time point is used in each case.

TABLE 3

| Example No. | $t_{50\%\ A}$ [min] in rat plasma |
|---|---|
| 1 | 60 |
| 2 | 30 |
| 3 | 55 |
| 4 | 1.7 |
| 5 | 8.0 |
| 6 | 1.1 |
| 7 | 0.5 |
| 9 | >120 |
| 10 | >120 |
| 12 | 2 |
| 13 | 0.5 |
| 14 | 0.5 | d) i.v. Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the tail vein using a Hamilton® glass syringe (bolus administration, duration of administration <10 s). Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life) and CL (clearance).

After i.v. administration of the compound from example 4, from example 5, from example 6 and from example 7, these substances were no longer detectable in plasma even at the first measurement point. Only the active ingredient (A) was detectable up to the 24-hour time point too.

e) Oral Pharmacokinetics in Wistar Rats:

On the day before administration of the substance, a catheter for obtaining blood is implanted in the jugular vein of the experimental animals (male Wistar rats, body weight 200-250 g) under Isofluran® anesthesia.

On the day of the experiment, a defined dose of the test substance is administered as solution into the stomach by gavage. Blood samples (8-12 time points) are taken through the catheter sequentially over the course of 24 h after administration of the substance. Plasma is obtained by centrifuging the samples in heparinized tubes. Acetonitrile is added to a defined plasma volume per time point to precipitate proteins. After centrifugation, test substance and, where appropriate, known cleavage products of the test substance in the supernatant are determined quantitatively using a suitable LC/MS-MS method.

The measured plasma concentrations are used to calculate pharmacokinetic parameters of the test substance and of the active ingredient compound (A) liberated therefrom, such as AUC, $C_{max}$, $T_{1/2}$ (half-life).

After oral administration of the compound from example 4, from example 5 and from example 6, these substances were no longer detectable in plasma even at the first measurement point. Only the active ingredient (A) was detectable up to the 24-hour time point too.

f) Determination of the Influence on the Heart Rate of Anesthetized Rats:

Male Wistar rats with a body weight above 250 g are employed. In the night before the experiment, the animals receive no feed but still have free access to drinking water. Preparation and investigations are carried out under Trapanal® anesthesia (100 mg/kg i.p.). Injection and infusion take place through a catheter in the jugular vein, and the blood pressure is recorded via a catheter in the femoral artery (transducer: Braun, Melsungen). After the preparation, the animals are connected to a continuous infusion of physiological saline solution to compensate fluid losses. Test substance or placebo solution are administered as bolus after an equilibration time of about 1 h. Heart rate and arterial blood pressure are recorded during the equilibration and over a period of at least 30 min after the bolus injection with the aid of a digital evaluation program.

Table 4 lists the maximum heart rate decrease in the first 30 min after an i.v. bolus of 100 µg/kg of the active substance (A) or of equivalent dosages of representative exemplary embodiments:

TABLE 4

| Example No. | Heart rate decrease [%] |
|---|---|
| A | 24 |
| 1 | 10 |
| 4 | 19 |
| 5 | 12 |
| 6 | 17 |
| 7 | 15 |

C. Exemplary Embodiments of Pharmaceutical Compositions

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.
Production:
The mixture of the compound of the invention, lactose and starch is granulated with a 5% strength solution (m/m) of PVP in water. The granules are dried and then mixed with the magnesium stearate for 5 min. This mixture is compressed with a conventional tablet press (see above for format of the tablet). As guideline, a compressive force of 15 kN is used for the compression.

Oral Suspension:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension are equivalent to a single dose of 100 mg of the compound of the invention.
Production:
The Rhodigel is suspended in ethanol, and the compound of the invention is added to the suspension. The water is added while stirring. The mixture is stirred for about 6 hours until the swelling of the Rhodigel is complete.

Oral Solution:
Composition:
500 mg of the compound of the invention, 2.5 g of polysorbate and 97 g of polyethylene glycol 400. A single dose of 100 mg of the compound of the invention corresponds to 20 g oral solution.
Production:
The compound of the invention is suspended in a mixture of polyethylene glycol and polysorbate with stirring. The stirring is continued until the compound of the invention has completely dissolved.

I.V. Solution:
The compound of the invention is dissolved in a concentration below the saturation solubility in a physiologically tolerated solvent (e.g. isotronic saline solution, 5% glucose solution and/or 30% PEG 400 solution, in each case adjusted to a pH of 3-5). The solution is optionally filtered sterile and/or dispensed into sterile and pyrogen-free injection containers.

The invention claimed is:
1. A compound of the formula (I)

in which
$R^4$ is a group of the formula in which
* means the point of linkage to the O atom,
$L^1$ and $L^2$ are independently of one another a bond or
—$CH_2$—, $R^1$, $R^2$ and $R^3$ are independently of one another hydrogen or methyl, $R^4$ and $R^6$ are identical or different and are independently of one another hydrogen or the side group of a natural α-amino acid or its homologs or isomers, $R^5$ and $R^7$ are independently of one another hydrogen or methyl, $L^3$ is straight-chain or branched $(C_2-C_4)$-alkanediyl which is additionally substituted by amino, $R^8$, $R^9$ and $R^{10}$ are independently of one another hydrogen or methyl, m is the number 2, 3, 4, 5 or 6, $L^4$ is straight-chain or branched $(C_2-C_4)$-alkanediyl, which is additionally substituted by carboxyl, $R^{11}$ is hydrogen or methyl, and n is the number 1, 2, 3 or 4, and the salts thereof.

2. The compound of the formula (I) as claimed in claim 1, in which $R^4$ is a group of the formula

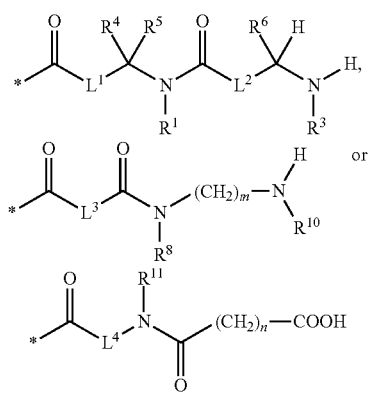

in which

* means the point of linkage to the O atom, $L^1$ is a bond, $L^2$ is a bond or —CH$_2$—, $R^1$ and $R^3$ are independently of one another hydrogen or methyl, $R^4$ is hydrogen, methyl, propan-2-yl, propan-1-yl, 2-methylpropan-1-yl, 1-methyl-propan-1-yl, butan-1-yl, benzyl, p-hydroxybenzyl, imidazol-4-ylmethyl, hydroxymethyl, 1-hydroxyethyl, carbamoylmethyl or 2-carbamoylethyl, $R^6$ is hydrogen, imidazol-4-ylmethyl, 4-aminobutan-1-yl, 3-aminopropan-1-yl, 2-aminoethyl, aminomethyl or 3-guanidinopropan-1-yl, $L^3$ is straight-chain $(C_2-C_4)$-alkanediyl which is additionally substituted by amino, $R^8$ and $R^{10}$ are independently of one another hydrogen or methyl, m is the number 2, 3 or 4, $L^4$ is straight-chain $(C_2-C_4)$-alkanediyl which is additionally substituted by carboxyl, $R^{11}$ is hydrogen or methyl, and n is the number 2, 3 or 4.

3. The compound of the formula (I) as claimed in claim 1, in which $R^4$ is a group of the formula

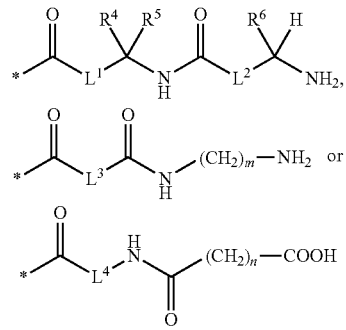

in which

* means the point of linkage to the O atom, $L^1$ and $L^2$ are each a bond, $R^4$ is hydrogen, methyl, propan-2-yl, propan-1-yl, 2-methylpropan-1-yl, 1-methyl-propan-1-yl, butan-1-yl, benzyl, p-hydroxybenzyl, imidazol-4-ylmethyl, hydroxymethyl, 1-hydroxyethyl, carbamoylmethyl or 2-carbamoylethyl, $R^6$ is imidazol-4-ylmethyl, 4-aminobutan-1-yl, 3-aminopropan-1-yl, 2-aminoethyl, aminomethyl or 3-guanidinopropan-1-yl, $L^3$ is a group of the formula —CH(NH$_2$)—CH$_2$—, —CH$_2$—CH(NH$_2$)—, —CH$_2$—CH(NH$_2$)—CH$_2$—, —CH(NH$_2$)—CH$_2$—CH$_2$— or —CH$_2$—CH$_2$—CH(NH$_2$)—, m is the number 2, 3 or 4, $L^4$ is a group of the formula —CH$_2$—CH(COOH)— or —CH$_2$—CH$_2$—CH(COOH)—, in which

** represents the point of linkage to the adjoining carbonyl group, and n is the number 2 or 3.

4. The compound of the formula (I) as claimed in claim 1, in which $R^4$ is a group of the formula

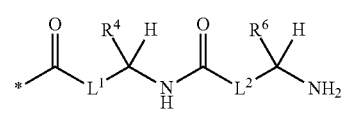

in which

* means the point of linkage to the O atom, $L^1$ and $L^2$ are each a bond, $R^4$ is hydrogen, methyl, propan-2-yl, 2-methylpropan-1-yl, benzyl, hydroxymethyl or 1-hydroxyethyl, and $R^6$ is imidazol-4-ylmethyl, 4-aminobutan-1-yl, 3-aminopropan-1-yl, 2-aminoethyl, aminomethyl or 3-guanidinopropan-1-yl.

5. The compound of the formula (I) as claimed in claim 1, in which
R⁴ is a group of the formula

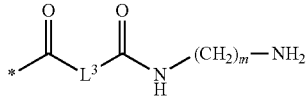

in which
* means the point of linkage to the O atom,
L³ is a group of the formula —CH(NH₂)—CH₂—, —CH₂—CH(NH₂)—, —CH(NH₂)—CH₂—CH₂— or —CH₂—CH₂—CH(NH₂)—,
and
m is the number 2 or 3.

6. A process for preparing compounds of the formula (I) as defined in claim 1, characterized in that the compound (A)

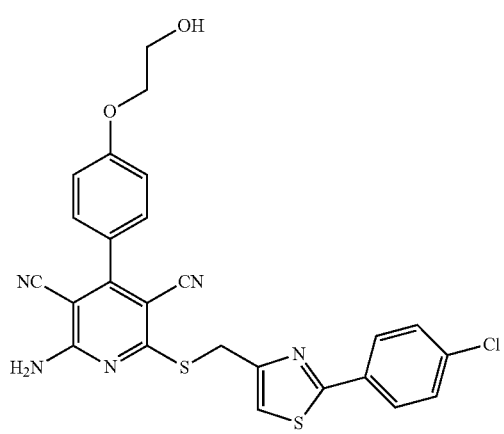

either
[A] is esterified in an inert solvent in the presence of a condensing agent initially with a carboxylic acid of the formula (II), (III) or (IV)

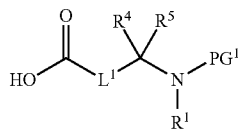

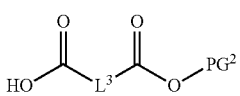

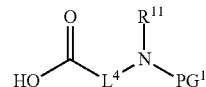

in which L¹, L³, L⁴, R¹, R⁴, R⁵ and R¹¹ each have the meanings indicated in claim 1, and
PG¹ is a temporary amino protective group such as, for example, tert-butoxycarbonyl
and
PG² is a temporary carboxyl protective group such as, for example, tert-butyl, to give compounds of the formula (V), (VI) or (VII),

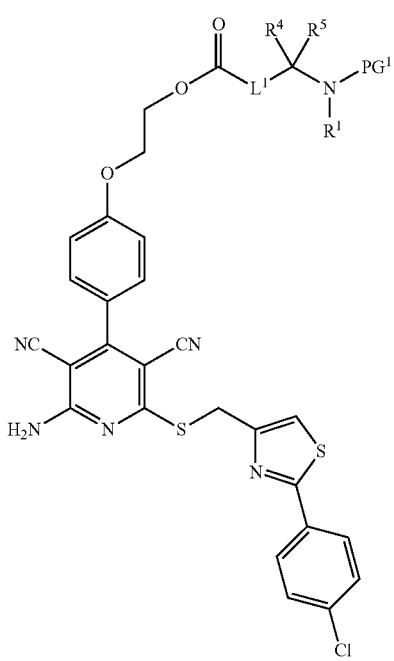

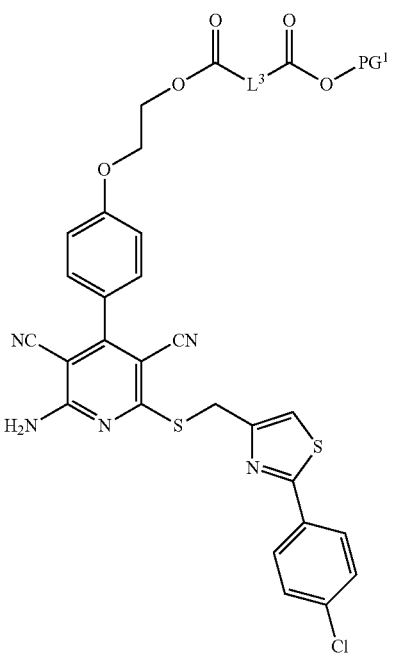

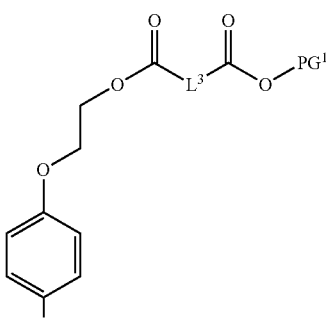

-continued (VII)

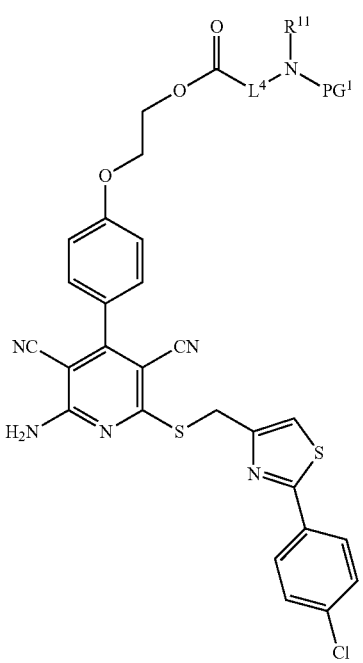

in which $L^1$, $L^3$, $L^4$, $R^1$, $R^4$, $R^5$, $R^{11}$, $PG^1$ and $PG^2$ each have the meanings indicated above, then, after elimination of the protective group $PG^1$ or $PG^2$, is coupled in an inert solvent in the presence of a condensing agent in the case of compound (V) with a compound of the formula (VIII), in the case of compound (VI) with a compound of the formula (IX) and in the case of compound (VII) with a compound of the formula (X)

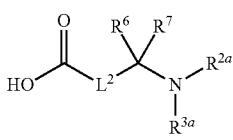
(VIII)

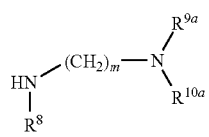
(IX)

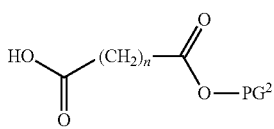
(X)

in which $L^2$, $R^6$, $R^7$, $R^8$, $PG^2$, m and n each have the meanings indicated in claim 1,
and
$R^{2a}$ and $R^{3a}$, and $R^{9a}$ and $R^{10a}$, are in each case identical or different and have the meanings of respectively $R^2$, $R^3$, $R^9$ and $R^{10}$ indicated in claims 1 to 5, or are a temporary amino protective group such as, for example, tert-butoxycarbonyl,
and subsequently protective groups which are present where appropriate are removed again,
or
[B] is coupled in an inert solvent in the presence of a condensing agent with a compound of the formula (XI), (XII) or (XIII)

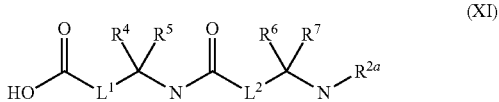
(XI)

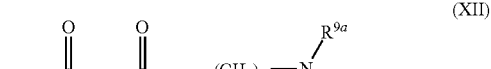
(XII)

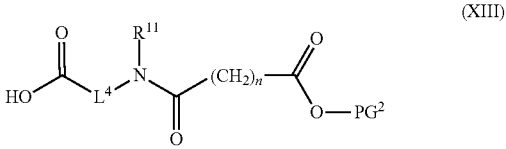
(XIII)

in which $L^1$, $L^2$, $L^3$, $L^4$, $R^1$, $R^4$, $R^5$, $R^6$, $R^7$, $R^8$, $R^{11}$, m and n each have the meanings indicated in claim 1,
$R^{2a}$ and $R^{3a}$, and $R^{9a}$ and $R^{10a}$, are in each case identical or different and have the meanings of respectively $R^2$, $R^3$, $R^9$ and $R^{10}$ indicated in claim 1, or are a temporary amino protective group such as, for example, tert-butoxycarbonyl,
and
$PG^2$ is a temporary carboxyl protective group such as, for example, tert-butyl,
and subsequently protective groups which are present where appropriate are removed again,
and the resulting compounds of the formula (I) are converted where appropriate with the appropriate (i) solvents and/or (ii) acids or bases into the solvates, salts and/or solvates of the salts thereof.

7. A medicament comprising a compound as defined in claim 1 in combination with one or more inert, non-toxic pharmaceutically suitable excipients.

8. A method for the treatment and/or prophylaxis of cardiovascular disorders in humans and animals by administering to a human or animal a compound as defined in claim 1.

* * * * *

UNITED STATES PATENT AND TRADEMARK OFFICE
CERTIFICATE OF CORRECTION

PATENT NO. : 8,703,696 B2
APPLICATION NO. : 12/671694
DATED : April 22, 2014
INVENTOR(S) : Lerchen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1118 days.

Signed and Sealed this

Twenty-ninth Day of September, 2015

Michelle K. Lee
*Director of the United States Patent and Trademark Office*